United States Patent
Kennedy et al.

(10) Patent No.: US 9,975,860 B2
(45) Date of Patent: May 22, 2018

(54) ANTI-ANGIOGENIC COMPOUNDS

(71) Applicants: UNIVERSITY COLLEGE DUBLIN—NATIONAL UNIVERSITY OF IRELAND, DUBLIN, Dublin (IE); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(72) Inventors: Breandan Kennedy, Dublin (IE); Alison Reynolds, Dublin (IE); Jacintha O'Sullivan, Dublin (IE); Andrew Douglas Baxter, Horsham (GB)

(73) Assignees: University College Dublin, National University of Ireland, Dublin, Dublin (IE); The Provost Fellows Foundation Scholars and the other members of the Board of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 0 days. days.

(21) Appl. No.: 15/111,865

(22) PCT Filed: Jan. 15, 2015

(86) PCT No.: PCT/EP2015/050710
§ 371 (c)(1),
(2) Date: Jul. 15, 2016

(87) PCT Pub. No.: WO2015/107122
PCT Pub. Date: Jul. 23, 2015

(65) Prior Publication Data
US 2016/0326122 A1    Nov. 10, 2016

(30) Foreign Application Priority Data

Jan. 17, 2014 (EP) .................................... 14151636

(51) Int. Cl.
*C07D 241/12* (2006.01)
*C07D 233/20* (2006.01)
*C07D 401/06* (2006.01)
*C07D 239/26* (2006.01)
*C07D 233/22* (2006.01)

(52) U.S. Cl.
CPC ......... *C07D 241/12* (2013.01); *C07D 233/20* (2013.01); *C07D 233/22* (2013.01); *C07D 239/26* (2013.01); *C07D 401/06* (2013.01)

(58) Field of Classification Search
CPC .. C07D 241/12; C07D 401/06; C07D 233/22; C07D 239/26
See application file for complete search history.

(56) References Cited

U.S. PATENT DOCUMENTS 4,971,986 A   11/1990  Stanek et al.
5,118,709 A    6/1992  Stanek et al.

FOREIGN PATENT DOCUMENTS

EP    0 335 832 A2      10/1989
WO    2006/044823   *    4/2006
WO    2006044823 A2     4/2006

OTHER PUBLICATIONS

Li, Zemin; Wu, Shikang, Inst. Photographic Chem., Chinese Academy of Sciences, Beijing, 100101, Peop. Rep. China. Journal of Fluorescence (1997), 13(1), 5-10.*
International Search Report issued in PCT/EP2015/050710; dated Apr. 21, 2015.
Banner et al.; Di- and Tri-methoxystyryl Derivatives of Heterocyclic Nitrogen Compounds; Arzneimittel Forschung. Drug Research; 1981; pp. 404-406; vol. 31; No. 3.
Gottfried Heinisch et al.; "Pyridazin-Analoga biologisch aktiver Verbindungen, 1. Mitt. trans-4-Styrylpyridazine"; Arch. Pharm.; 1980; pp. 53-60; vol. 313; Verlag Chemie. GmbH. Weinheim.
Nikzad Nikbin et al.; "Continuous Flow Ligand-Free Heck Reactions Using Monolithic Pd [0] Nanoparticles"; Organic Process Research & Development; 2007; pp. 458-462; vol. 11; No. 3; American Chemical Society.
Stanek et al.; "S-Adenosylmethionine Decarboxylase Inhibitors: New Aryl and Heteroaryl Analogues of Methylglyoxal Bis(guanylhydrazone)"; Journal of Medicinal Chemistry; 1993; pp. 46-54; vol. 36; No. 1; American Chemical Society.
Wen-Der Lu et al.; "Substituent effect on anionic cycloaromatization of 2-(2-substituted ethynyl)benzonitriles and related molecules"; Tetrahedron; 2002; pp. 7315-7319; vol. 58; Elsevier Science Ltd.
R. Franke; "Einwirkung von 2.5-Dimethylpyrazin auf Aldehyde"; Aus dem chemischen Institut in Breslau; 1905; pp. 3724-3728.
Zemin Li et al.; "The Effect of Molecular Structure on the Photophysical Behavior of Substituted Styryl Pyrazine Derivatives"; Journal of Fluorescence; 1997; pp. 237-242; vol. 7; No. 3; Plenum Publishing Corporation.
Akihiro Ohta et al.; "Photocyclization of Styrylpyrazines"; Chemical & Pharmaceutical Bulletin; 1979; pp. 2596-2601; vol. 27; No. 11.
Written Opinion issued in PCT/EP2015/050710; dated Apr. 21, 2015.

* cited by examiner

*Primary Examiner* — Alexander R Pagano
*Assistant Examiner* — Ebenezer O Sackey
(74) *Attorney, Agent, or Firm* — Studebaker & Brackett PC

(57) ABSTRACT

Compounds and compositions are described which are useful especially for treatment of angiogenesis-related diseases or disorders such as neovascularisation of the eye, age-related macular degeneration, diabetic retinopathy or cancer.

10 Claims, 20 Drawing Sheets

ANTI-ANGIOGENIC COMPOUNDS

INTRODUCTION

The invention relates to anti-angiogenic compounds.

In many human diseases there is an inappropriate growth of new blood vessels (angiogenesis). Angiogenesis is a physiological process involving the growth of new blood vessels from pre-existing vessels (Ferrara and Kerbel, 2005). Angiogenesis may be a therapeutic target for combating diseases characterised by poor vascularisation or abnormal vasculature (Ferrara and Kerbel, 2005). Targeted administration of specific compounds that may inhibit (anti-angiogenesis) or induce (pro-angiogenesis) the creation of new blood vessels in the body may help combat such diseases.

Diabetic retinopathy (DR) is the most feared complication of diabetes, compromising the quality of life in most sufferers (Frank, 2004). About 30% of type 1 diabetes patients advance to the blinding stage of the disease and about 60% of type 2 diabetes patients develop retinopathy. DR is the most common cause of vision impairment in people of working age in Western society and is likely to increase in prevalence as it has been projected that about 360 million people will suffer from diabetes by 2030. Diabetic macular oedema is the principal cause of vision loss in diabetes and involves leakage from a disrupted blood-retinal barrier.

Age-related macular degeneration (AMD) is a leading cause of vision loss in the western world among people aged 50 or older (Rattner and Nathans, 2006; Jager et al., 2008). Ninety percent of vision loss due to AMD results from the exudative form, which is characterized by newly formed blood vessels arising from capillaries in the choroid layer adjacent to the retina.

Current approaches for resolving inappropriate growth of new vessels in the eye include laser treatment and molecular therapies targeted to vascular endothelial cell growth factor (VEGF) (Ferrara, Rattner and Nathans, 2006; Jager et al., 2008).

Photodynamic therapy (PDT) is a laser-based surgery for wet age-related macular degeneration. In PDT a light-sensitive dye is injected intravenously. A low energy laser beam is directed onto the target vessels. This makes the chemical react and destroy the leaking blood vessels without damaging adjacent healthy tissue however, multiple treatments are usually required and PDT is unsuitable for long-established wet age-related macular degeneration and cannot restore sight already lost to age-related macular degeneration.

There are a number of variations of VEGF molecular therapy but those in clinical use are antibodies or decoy receptors targeted to VEGF which stop the development of new leaky blood vessels. Treatment requires intraocular injection by retinal specialists, needs to be repeated every six weeks and requires the patient to be sedated. In some cases, VEGF treatment has been shown to restore some visual acuity.

In diabetic retinopathy, laser ablation of the new vessels is routinely performed however laser ablation locally destroys the retina. In age-related macular degeneration monoclonal antibodies or decoy receptors attenuating VEGF signalling are used clinically (Macugen, Lucentis, Eylea), however the monoclonal antibodies and decoy receptors are very expensive to manufacture/administer and patients require monthly intravitreal injections (Narayanan et al., 2006). Armala (pazopanib) is a multi-kinase (VEGF, PDGF, c-kit) angiogenesis inhibitor in clinical trials for AMD and cancer (Takahashi et al., 2009). siRNA targeting VEGF have also been used in clinical trials, however the siRNAs to VEGF have been found to act by a non-specific mechanism (Kleinman et al., 2008).

Cancer can originate in many tissues including the bowel, breast and skin. Obviously, with the prevalence and incurability of cancer types, there is a real need to develop new therapeutics. It is now widely accepted that the growth of solid tumours is dependent on their capacity to acquire a blood supply (Bergers and Benjamin, 2003). Indeed, much effort has been directed towards the development of anti-angiogenics that disrupt this process in tumours. In contrast to traditional anti-cancer agents that directly destroy tumour cells, mediating a cytocidal effect, anti-angiogenics are generally regarded as cytostatic agents. Another emerging feature of the use of anti-angiogenics in cancer treatment is the phenomenon of resistance (Bergers and Hanahan, 2008). In both animal models and humans, the benefits of anti-angiogenic therapy are at best transitory and commonly followed by a restoration of tumour growth and progression. As such, there is a pressing need to find multiple target points for anti-angiogenic therapy, so as to provide additional opportunities to pre-empt such resistance phenomena emerging.

Of particular relevance is Colorectal Cancer (CRC) which accounts for 10-15% of all cancers and is the leading cause of cancer deaths in the Western world (Mandala et al., 2004). Colorectal cancer is the commonest internal cancer in the Western World. It is a major cause of morbidity and mortality, with approximately 50 percent dying from their disease within 5 years of diagnosis. Contemporary chemotherapy treatments are effective in many cases but extremely expensive and potentially dangerous.

Current treatments for colorectal cancer patients are complex. Multidisciplinary teams must decide who will benefit from expensive new treatments. Currently, treatment decisions for patients depend solely on pathological staging. The chemotherapeutic agents Fluorouracil (5-FU) plus leucovorin (LV) have been the mainstay treatment for CRC. Newer drugs such as oxaliplatin, capecitabine and irinotecan have significantly improved response rates, time to progression and increase survival rates in patients with advanced CRC (Mandala et al., 2004). However, even with these new drug combinations, the long term prognosis remains poor for late-stage CRC patients with metastatic lesions.

Over the last few years, new monoclonal antibody therapies targeting key angiogenic molecules including: bevacizumab (Avastin, anti-VEGF) and cetuximab (Erbitux, anti-EGFR) (Culy, 2005; He and Marshall, 2005) have been introduced to fight late-stage CRC and improve outcome (Ellis, 2003). Bevacizumab (Avastin) blocks vascular endothelial growth factor (VEGF) by preventing the interaction of VEGF with its' receptors [VEGFR-1 (Flt-1) and VEGFR-2 (KDR)]. Pre-clinical studies suggest that bevacizumab acts by inhibiting tumour neo-vascularisation and when used in combination with chemotherapeutic drugs, it increases the permeability of tumours to chemotherapy (Ellis, 2003). Cetuximab (Erbitux) inhibits the epidermal growth factor receptor (EGFR) signalling cascade (Wong, 2005) and tumours that over-express EGFR have a poor prognosis. Erbitux also inhibits angiogenesis inside tumours, leading to an overall suppression of tumour growth (Carmeliet, 2005). Pre-clinical data indicate that Erbitux has anti-tumour activity in colon cancer xenografts and can reduce the production of VEGF, interleukin-8 (IL-8), and basic fibroblast growth factor (bFGF). Currently, these molecular therapies are solely given to late-stage metastatic CRC patients

STATEMENTS OF INVENTION

According to the invention there is provided a pharmaceutical composition comprising a compound of the formula:

A-X—Y—B wherein A is a six membered heteroaryl ring containing 2 nitrogen atoms which is optionally substituted with R1;

R1 is H, C1-6 alkyl, CN, CONR2R3;

R2 and R3 which may be the same or different and selected from H, C1-6 alkyl or R2 and R3 form a ring;

the group X—Y is an alkyne or alkene, in the case wherein X—Y is an alkene the double bond may be cis or trans and optionally substituted with R1

B is an aryl; or five or six membered heteroaryl ring containing 1 to 3 heteroatoms, both of which may optionally substituted with one or more R4;

R4 is R1 or OR5;

R5 is H, COR6 or R6; and

R6 is C1-6 alkyl and salts thereof.

In one embodiment R1 is H or C1-6 alkyl. In one case R1 is CH3.

In one embodiment X—Y is an alkyne.

In another embodiment X—Y is an alkene which is optionally substituted with R1. In one case R1 is CH3.

In one embodiment B is an aryl which may be optionally substituted with one or more R4. In one case R4 is OR5. In one case R5 is H. In one case R4 is at the 2 position of the aryl ring.

In one embodiment B is phenol.

The compound may be selected from one or more of

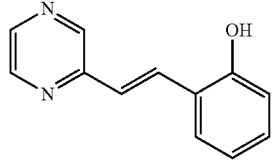 [SMILES: Oc1ccccc1/C=C/c1cnccn1]

(E)-2-(2-(Pyrazin-2-yl)vinyl]phenol

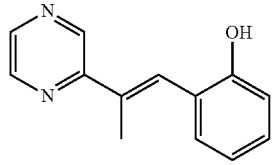 [SMILES: C/C(=C\c1ccccc1O)c1cnccn1]

(E)-2-[2-(Pyrazin-2-yl)prop-1-enyl]phenol

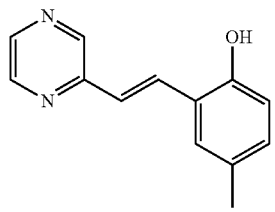 [SMILES: Cc1ccc(O)c(/C=C/c2cnccn2)c1]

(E)-4-Methyl-[2-(2-(Pyrazin-2-yl)vinyl)]phenol

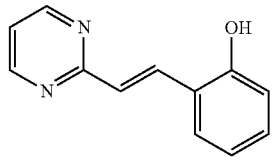 [SMILES: Oc1ccccc1/C=C/c1ncccn1]

(E)-2-[2-(Pyrimidin-2-yl)vinyl]phenol

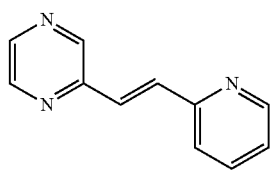 [SMILES: C(=C\c1cnccn1)/c1ccccn1]

(E)-2-[2-(Pyridin-2-yl)vinyl)pyrazine

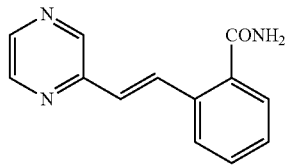 [SMILES: NC(=O)c1ccccc1/C=C/c1cnccn1]

(E)-2-[2-(Pyrazin-2-yl)vinyl)benzamide

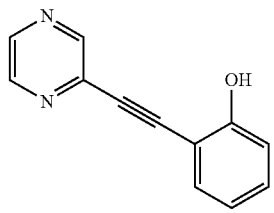 [SMILES: Oc1ccccc1C#Cc1cnccn1]

2-[2-(Pyrazin-2-yl)ethynyl]phenol

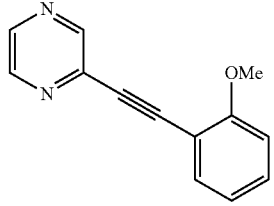

2-[2-(2-Methoxyphenyl) ethynyl]pyrazine

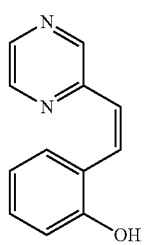

(Z)-2-[2-(Pyrazin-2-yl)vinyl]phenol

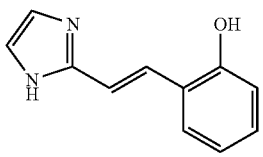 [SMILES: Oc1ccccc1/C=C/c1ncc[nH]1]

(E)-2-(2-(1H-imidazol-2-yl)vinyl)phenol; and

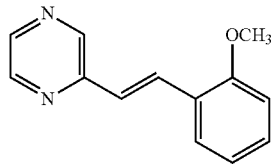 [SMILES: COc1ccccc1/C=C/c1cnccn1]

2-[2-(2-methoxyphenyl)ethenyl] pyrazine
and salts thereof such as the HCl salt.

The composition may further comprise a pharmaceutically acceptable excipient.

In one case the composition is in a form for topical administration.

The composition may be in the form of eye drops.

The composition may be in a form for systemic administration.

The composition may be in the form of an injectable solution or suspension.

The composition may be for use in the treatment of an angiogenesis-related disease or disorder.

The invention also provides use of a composition as defined in the treatment of an angiogenesis-related disease or disorder.

The angiogenesis-related disease or disorder may be associated with neovascularisation of the eye. The angiogenesis-related disease or disorder may be associated with blindness.

The angiogenesis-related disease or disorder may be age-related macular degeneration or diabetic retinopathy. The age-related macular degeneration may be wet age-related macular degeneration.

In one embodiment the angiogenesis-related disease or disorder is cancer. The cancer may be a solid tumour forming cancer. The cancer may be colorectal cancer. The cancer may be oesophageal cancer. The cancer may be breast cancer.

Also provided is a compound as defined above for use in treating cancer. The cancer may be a solid tumour forming cancer. The cancer may be colorectal cancer. The cancer may be oesophageal cancer. The cancer may be breast cancer.

The invention also provides a compound selected from

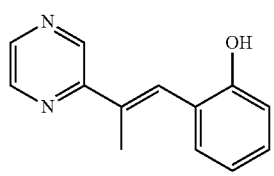 [SMILES: C/C(=C\c1ccccc1O)c1cnccn1]

(E)-2-[2-(Pyrazin-2-yl)prop-1-enyl]phenol

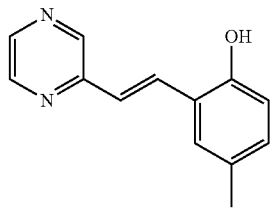 [SMILES: Cc1ccc(O)c(/C=C/c2cnccn2)c1]

(E)-4-Methyl-[2-(2-(Pyrazin-2-yl)vinyl)]phenol

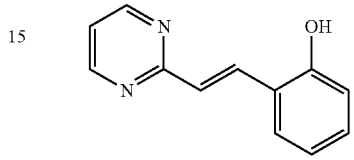

(E)-2-[2-(Pyrimidin-2-yl)vinyl]phenol

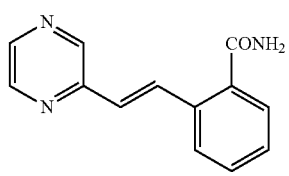 [SMILES: NC(=O)c1ccccc1/C=C/c1cnccn1]

(E)-2-[2-(Pyrazin-2-yl)vinyl)benzamide

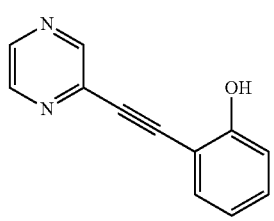 [SMILES: Oc1ccccc1C#Cc1cnccn1]

2-[2-(Pyrazin-2-yl)ethynyl]phenol

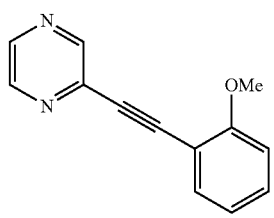

2-[2-(2-Methoxyphenyl) ethynyl]pyrazine

According to the invention there is provided a compound of the formula:

A-X—Y—B wherein A is a five or six membered heteroaryl ring containing 1 to 3 heteroatoms, optionally substituted with R1;

R1 is H, C1-6 alkyl, CN, CONR2R3;

R2 and R3 which may be the same or different and selected from H, C1-6 alkyl or R2 and R3 form a ring;

the group X—Y is an alkyne or alkene, in the case wherein X—Y is an alkene the double bond may be cis or trans and optionally substituted with R1

B is an aryl; or five or six membered heteroaryl ring containing 1 to 3 heteroatoms, both of which may optionally substituted with one or more R4;

R4 is R1 or OR5;

R5 is H, COR6 or R6; and

R6 is C1-6 alkyl and salts thereof.

In one embodiment A us a six membered heteroaryl ring containing 1 to 3 heteroatoms which is optionally substituted with R1. A may be six membered heteroaryl ring containing 1 to 3 nitrogen atoms which is optionally substituted with R1. A may be a six membered heteroaryl ring containing 2 nitrogen atoms which is optionally substituted with R1. In some cases, R1 is H or C1-6 alkyl. In one embodiment R1 is CH3.

In some cases A is not a fused Ring. In some embodiments the compounds are not quinolones.

In one embodiment X—Y is an alkyne.

In another embodiment X—Y is an alkene which is optionally substituted with R1. R1 may, for example be CH3.

In some embodiments B is an aryl which may be optionally substituted with one or more R4. In some cases R4 is OR5. R5 may, for example be H. In one case R4 is at the 2 position of the aryl ring.

In some embodiments B is phenol.

The compound may selected from

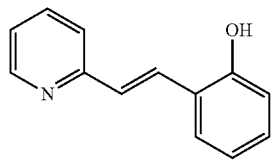 [SMILES: Oc1ccccc1/C=C/c1ccccn1]

(E)-2-[2-(Pyridin-2-yl)vinyl]phenol

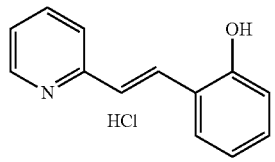 [SMILES: Oc1ccccc1/C=C/c1ccccn1 ; Cl]

(E)-2-[2-(Pyridin-2-yl)vinyl]phenol hydrochloride

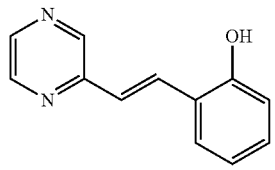 [SMILES: Oc1ccccc1/C=C/c1cnccn1]

(E)-2-(2-(Pyrazin-2-yl)vinyl]phenol

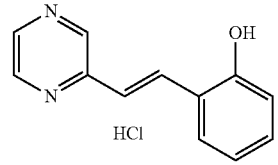 [SMILES: Oc1ccccc1/C=C/c1cnccn1 ; Cl]

(E)-2-[2-(Pyrazin-2-yl)vinyl]phenol hydrochloride

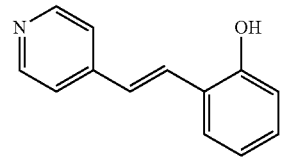 [SMILES: Oc1ccccc1/C=C/c1ccncc1]

(E)-2-[2-(Pyridin-4-yl)vinyl]phenol

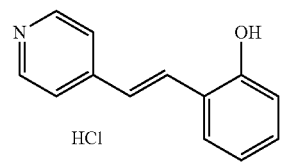 [SMILES: Oc1ccccc1/C=C/c1ccncc1 ; Cl]

(E)-2-[2-(Pyridin-4-yl)vinyl]phenol hydrochloride

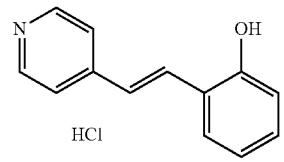 [SMILES: Oc1ccccc1/C=C/c1ccncc1 ; Cl]

(E)-2-[2-(6-Methylpyridin-2-yl)vinyl]phenol

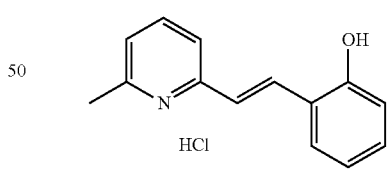

(E)-2-[2-(6-Methylpyridin-2-yl)vinyl]phenol hydrochloride

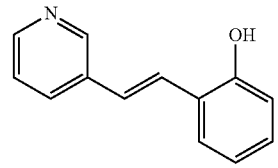 [SMILES: Oc1ccccc1/C=C/c1cccnc1]

(E)-2-[2-(Pyridin-3-yl)vinyl]phenol

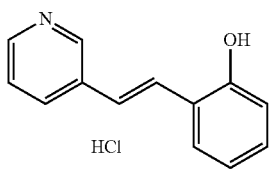 [SMILES: Oc1ccccc1/C=C/c1cccnc1 ; Cl]

(E)-2-[2-(Pyridin-3-yl)vinyl]phenol hydrochloride

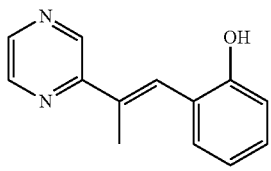 [SMILES: C/C(=C\c1ccccc1O)c1cnccn1]

(E)-2-[2-(Pyrazin-2-yl)prop-1-enyl]phenol

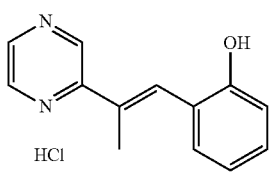 [SMILES: C/C(=C\c1ccccc1O)c1cnccn1 ; Cl]

((E)-2-[2-(Pyrazin-2-yl)prop-1-enyl]phenol hydrochloride

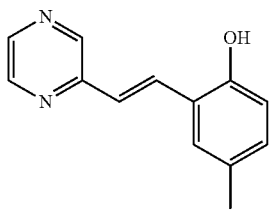 [SMILES: Cc1ccc(O)c(/C=C/c2cnccn2)c1]

(E)-4-Methyl-[2-(2-(Pyrazin-2-yl)vinyl)]phenol

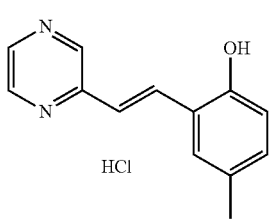

(E)-4-Methyl-[2-(2-(Pyrazin-2-yl)vinyl)]phenol hydrochloride

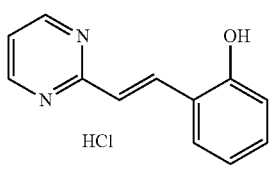 [SMILES: Oc1ccccc1/C=C/c1ncccn1 ; Cl]

(E)-2-[2-(Pyrimidin-2-yl)vinyl]phenol hydrochloride

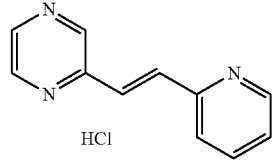 [SMILES: C(=C\c1cnccn1)/c1ccccn1 ; Cl]

(E)-2-[2-(Pyridin-2-yl)vinyl)pyrazine hydrochloride

(E)-2-[2-(Pyrazin-2-yl)vinyl)benzamide hydrochloride

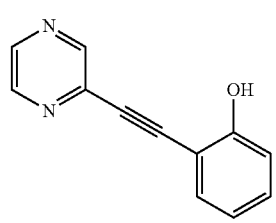 [SMILES: Oc1ccccc1C#Cc1cnccn1]

2-[2-(Pyrazin-2-yl)ethynyl]phenol

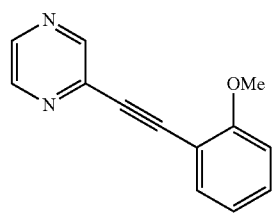

2-[2-(2-Methoxyphenyl) ethynyl]pyrazine

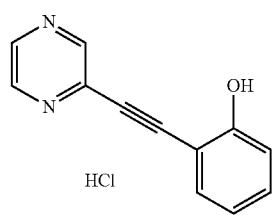 [SMILES: Oc1ccccc1C#Cc1cnccn1 ; Cl]

2-[2-(Pyrazin-2-yl)ethynyl]phenol hydrochloride

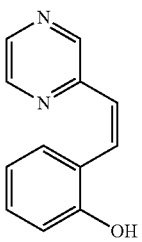

(Z)-2-[2-(Pyrazin-2-yl)vinyl]phenol

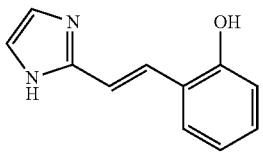 [SMILES: Oc1ccccc1/C=C/c1ncc[nH]1]

(E)-2-(2-(IH-imidazol-2-yl)vinyl)phenol; and

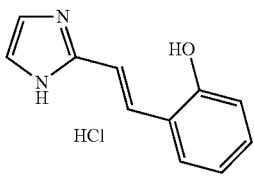 [SMILES: Oc1ccccc1/C=C/c1ncc[nH]1 ; Cl]

(E)-2-(2-(IH-imidazol-2-yl)vinyl)phenol hydrochloride

The invention also provides a compound of the formula:

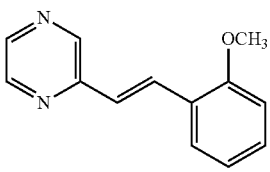 [SMILES: COc1ccccc1/C=C/c1cnccn1]

and salts thereof for use as a medicament, for example for use in the treatment of an angiogenesis-related disease or disorder.

The compounds may be for use in the treatment of an angiogenesis-related disease or disorder.

The angiogenesis-related disease or disorder may be associated with neovascularisation of the eye. The angiogenesis-related disease or disorder may be associated with blindness. In one case the angiogenesis-related disease or disorder is age-related macular degeneration or diabetic retinopathy. The age-related macular degeneration may be wet age-related macular degeneration.

In another embodiment the angiogenesis-related disease or disorder is cancer. The cancer may be a solid tumour forming cancer. The cancer may be colorectal cancer. The cancer may be oesophageal cancer. The cancer may be breast cancer.

The invention also provides pharmaceutical composition comprising one or more compounds as defined.

The composition may further comprise a pharmaceutically acceptable excipient. The composition may be in a form for topical administration. The composition may be in the form of eye drops. The composition may be in a form for systemic administration. The composition may be in the form of an injectable solution or suspension.

The compounds and compositions of the invention may also be used for redirecting metabolism rates and/or DNA expression of repair proteins in cancer cells.

The compounds and compositions of the invention may also be used as an adjunct treatment to radiation or other cancer treatments.

The compounds and compositions of the invention may be useful in the treatment of oesophageal cancer—such as oesophageal adenocarcinoma as well as other cancers including colorectal cancer and breast cancer.

The compounds and compositions of the invention may be administered by any conventional route for example parenterally such as in the form of an injectable solution or suspension, enterally for example orally such as in the form of an oral dosage form for example a tablet or a capsule, or topically for example in the form of lotions, gels, ointments, creams or eyedrops. The compounds or compositions of the invention may also be administered in a nasal or suppository form. The route of administration of the compounds and compositions of the invention will depend on the angiogenic driven disease (angiogenic-related disease or disorder) and/or the undesirable inflammation to be treated.

It will be appreciated by a person skilled in the art that the compounds and compositions of the invention should be administered in a therapeutically effective amount. The dosage of the active ingredient will depend on a variety of factors including type, species, age, weight, sex, medical condition of the patient, the severity of the condition to be treated and the route of administration.

BRIEF DESCRIPTION OF THE DRAWINGS

The invention will be more clearly understood from the following description of embodiments thereof, given by way of example only, with reference to the accompanying Figures, in which.

DETAILED DESCRIPTION

Figure 1A:
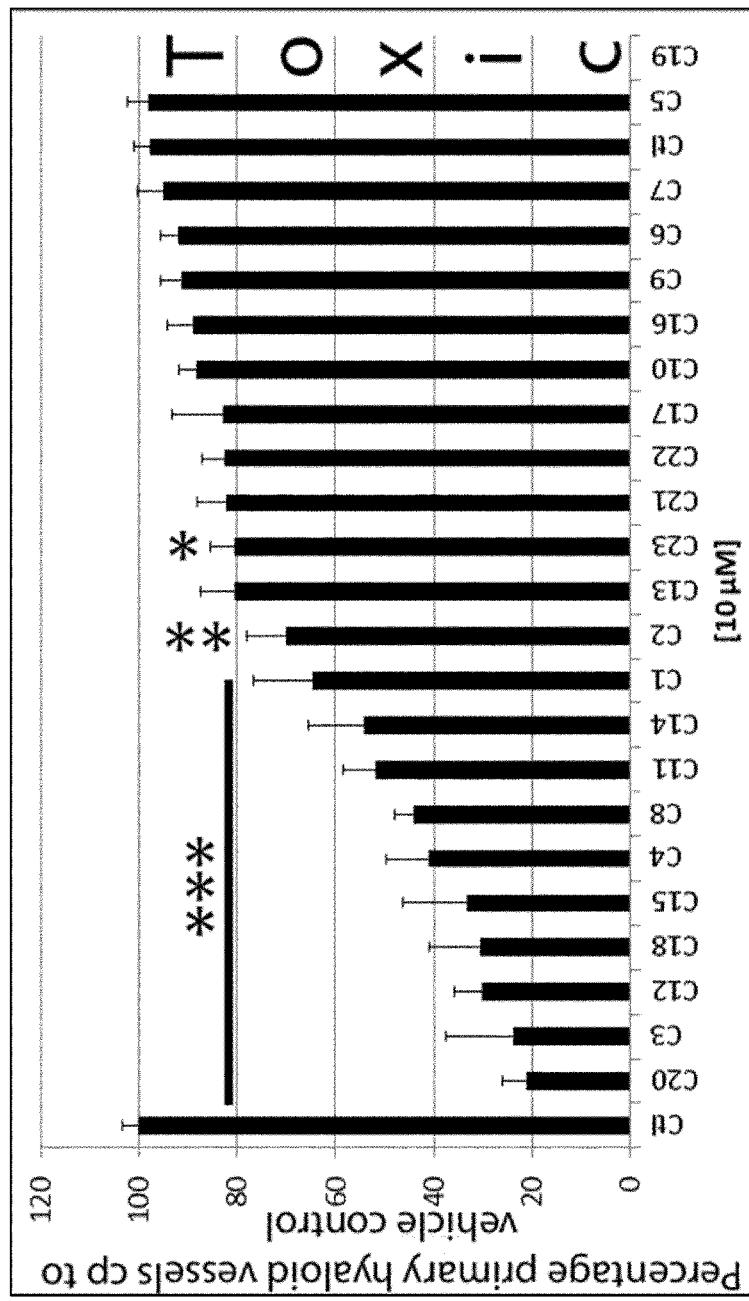
FIG. 1A is a graph showing the effect of 10 µM of tested compounds on inhibiting developmental angiogenesis of the primary hyaloid vessels in zebrafish. n>=12, *p-value≤0.001, p-value≤0.01, *p-value≤0.05. Data shown is mean+SEM and expressed as a percentage of the vehicle control.

General Procedure for the Preparation of Compounds 1-15

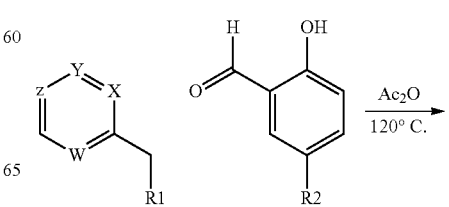

-continued

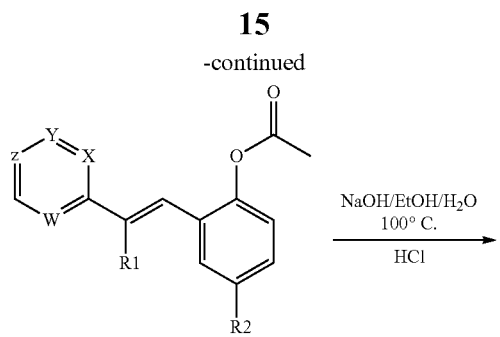

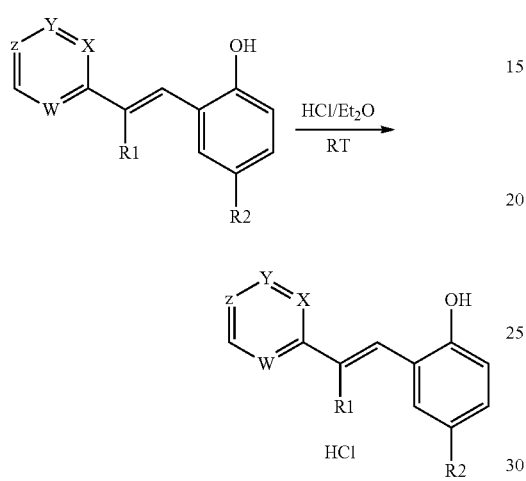

Alternative Procedure for the Preparation of Compounds 1-15

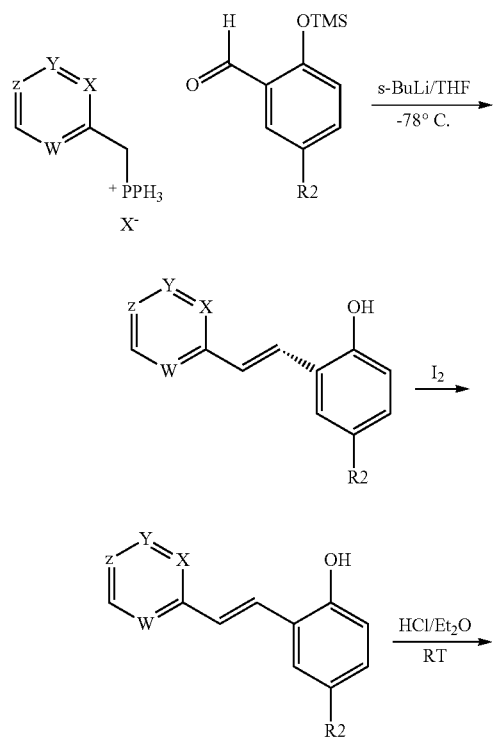

-continued

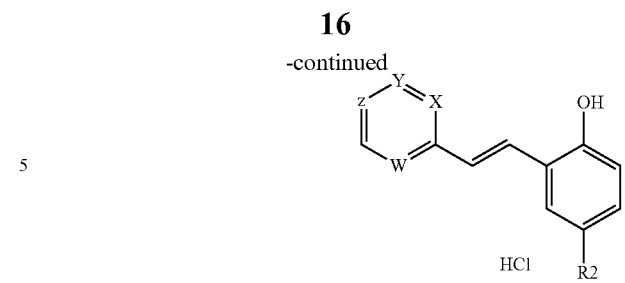

EXPERIMENTAL

Intermediate 1: (E)-2-[2-(Pyrazin-2-yl)vinyl]phenyl acetate

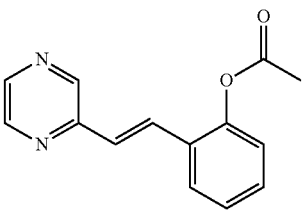 [SMILES: CC(=O)Oc1ccccc1/C=C/c1cnccn1]

2-Methylpyrazine (0.91 mL, 0.94 g, 10.0 mmol, 1.0 eq.) and 2-hydroxybenzaldehyde (1.05 mL, 1.22 g, 10.0 mmol, 1.0 eq.) were dissolved in acetic anhydride (1.89 mL, 2.04 g, 20.0 mmol, 2.0 eq.) and the resulting mixture was heated at 120-140° C. for 4 days. The mixture was allowed to cool down to room temperature then poured onto water (100 mL) and stirred vigorously for 1 h. The mixture was extracted with ethyl acetate (3×50 mL). The combined organic extracts were then washed with brine (50 mL), dried over sodium sulfate and concentrated in vacuo. The crude product was purified by column chromatography (SiO$_2$, 1:1 ethyl acetate-cyclohexane) providing (E)-2-[2-(pyrazin-2-yl)vinyl]phenyl acetate (1.14 g, 47% yield) as a yellow solid. Similarly prepared was:

Intermediate 2: (E)-2-[2-(Pyrazin-2-yl)prop-1-enyl] phenyl acetate

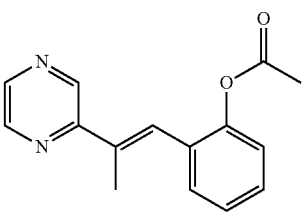 [SMILES: CC(=O)Oc1ccccc1/C=C(\C)c1cnccn1]

From 2-Ethylpyrazine (1.02 mL, 1.00 g, 9.2 mmol, 1.0 eq.) and 2-hydroxybenzaldehyde (1.46 mL, 1.69 g, 13.9 mmol, 1.5 eq.); isolated as a clear yellow oil which was used in the next stage without purification.

Intermediate 3: (E)-4-Methyl-[2-(2-(pyrazin-2-yl)vinyl)]phenyl acetate

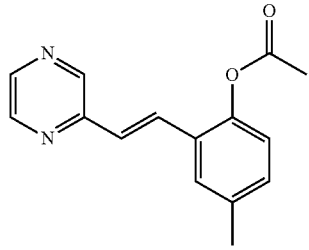 [SMILES: CC(=O)Oc1ccc(C)cc1/C=C/c1cnccn1]

From 2-Methylpyrazine (0.56 mL, 0.58 g, 6.1 mmol, 1.0 eq.) and 2-hydroxy-5-methylbenzaldehyde (1.0 g, 7.3 mmol, 1.2 eq.); isolated as a clear orange oil (0.53 g, 34% yield).

Intermediate 4: (E)-2-[2-(Pyrimidin-2-yl)vinyl]phenyl acetate

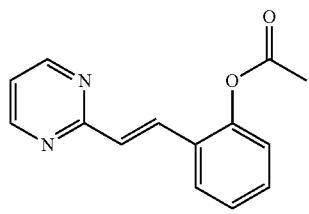 [SMILES: CC(=O)Oc1ccccc1/C=C/c1ncccn1]

From 2-Methylpyrimidine (0.30 mL, 0.30 g, 3.2 mmol, 1.0 eq.) and 2-hydroxybenzaldehyde (0.34 mL, 0.39 g, 3.2 mmol, 1.0 eq.); isolated as a yellow solid (0.57 g, 74% yield).

Intermediate 5: (E)-2-[2-(Pyridin-2-yl)vinyl]phenyl acetate

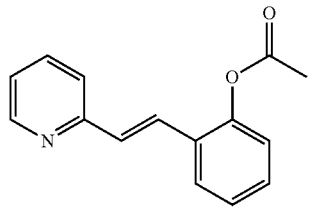 [SMILES: CC(=O)Oc1ccccc1/C=C/c1ccccn1]

From 2-Methylpyridine (0.99 mL, 0.93 g, 10.0 mmol, 1.0 eq.) and 2-hydroxybenzaldehyde (1.05 mL, 1.22 g, 10.0 mmol, 1.0 eq.); isolated as a yellow solid (1.74 g, 72% yield).

Intermediate 6: (E)-2-[2-(Pyridin-4-yl)vinyl]phenyl acetate

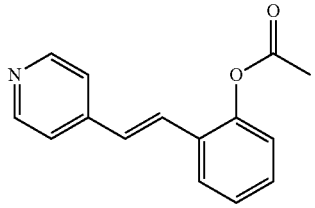 [SMILES: CC(=O)Oc1ccccc1/C=C/c1ccncc1]

From 4-Methylpyridine (0.97 mL, 0.93 g, 10.0 mmol, 1.0 eq.) and 2-hydroxybenzaldehyde (1.05 mL, 1.22 g, 10.0 mmol, 1.0 eq.); isolated as a yellow solid (1.67 g, 70% yield).

Intermediate 7: (E)-2-[2-(Pyridin-3-yl)vinyl]phenyl acetate

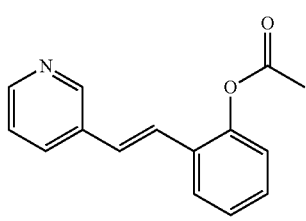 [SMILES: CC(=O)Oc1ccccc1/C=C/c1cccnc1]

From 3-Methylpyridine (0.99 mL, 0.93 g, 10.0 mmol, 1.0 eq.) and 2-hydroxybenzaldehyde (1.05 mL, 1.22 g, 10.0 mmol, 1.0 eq.); isolated as an orange solid (1.64 g, 69% yield).

Intermediate 8: (E)-2-[2-(6-Methylpyridin-2-yl)vinyl]phenyl acetate

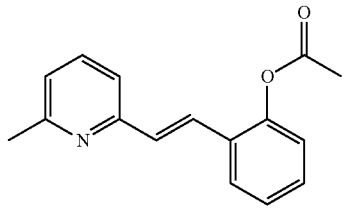 [SMILES: CC(=O)Oc1ccccc1/C=C/c1cccc(C)n1]

From 2,6-Dimethylpyridine (1.16 mL, 1.07 g, 10.0 mmol, 1.0 eq.) and 2-hydroxybenzaldehyde (1.05 mL, 1.22 g, 10.0 mmol, 1.0 eq.); isolated as a clear pale yellow oil (0.64 g, 25% yield).

Intermediate 9: (E)-2-[2-(1H-Imidazol-2-yl)vinyl]phenyl acetate

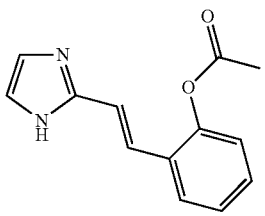 [SMILES: CC(=O)Oc1ccccc1/C=C/c1ncc[nH]1]

From 2-methylimidazole (10.08 g, 123 mmol, 1.0 eq.) and 2-hydroxybenzaldehyde (15 g, 0.123 mmol, 1.0 eq.); isolated as a brown oil which was used without purification in the next stage.

Compound 1: (E)-2-[2-(Pyridin-2-yl)vinyl]phenol

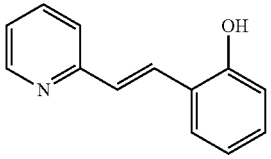 [SMILES: Oc1ccccc1/C=C/c1ccccn1]

(E)-2-[2-(Pyridin-2-yl)vinyl]phenyl acetate [Intermediate 5; 1.7 g, 7.0 mmol, 1.0 eq.)] was dissolved in ethanol (85 mL) and aqueous NaOH (5%, 7.0 mL) and water (68 mL) were added. The resulting mixture was heated at 100° C. for 15 min. The mixture was then allowed to cool down to room temperature and neutralised by careful addition of aqueous HCl (10%). The mixture was kept at −18° C. in the freezer over night, the resulting solids were filtered off and dried in vacuo providing (E)-2-[2-(pyridin-2-yl)vinyl]phenol (0.91 g, 66%) as an off-white solid; $^1$H NMR (400 MHz, DMSO-$d_6$) δ 6.82 (t, J=7.5 Hz, 1H, Ar), 6.89 (d, J=8.0 Hz, 1H, Ar), 7.13 (t, J=7.5 Hz, 1H, Ar), 7.21 (m, 1H, Ar), 7.27 (d, J=16.0 Hz, 1H, C=CH), 7.47 (d, J=8.0 Hz, 1H, Ar), 7.61 (d, J=7.5 Hz, 1H, Ar), 7.75 (d, J=7.5 Hz, 1H, Ar), 7.92 (d, J=16.0 Hz, 1H, C=CH), 9.88 (br s, 1H, OH).

Compound 2: (E)-2-[2-(Pyridin-2-yl)vinyl]phenol hydrochloride

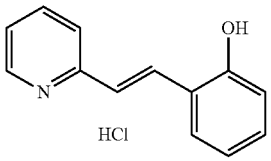 [SMILES: Oc1ccccc1/C=C/c1ccccn1 ; Cl]

A solution of hydrochloric acid (2.0 M in diethyl ether, 0.24 mL, 0.47 mmol, 1.0 eq.) was added dropwise to a stirred suspension of (E)-2-[2-(pyridin-2-yl)vinyl]phenol [Compound 1; (100 mg, 0.47 mmol, 1.0 eq.)] in dry diethyl ether (5 mL). The resulting suspension was stirred at room temperature for 30 min and the solid removed by filtration. The product was washed with diethyl ether (2×5 mL) and dried in vacuo providing (E)-2-[2-(pyridin-2-yl)vinyl]phenol hydrochloride as a yellow solid (94 mg, 80% yield); $^1$H NMR (400 MHz, DMSO-$d_6$) δ 6.81 (t, J=7.5 Hz, 1H, Ar), 6.88 (d, J=8.0 Hz, 1H, Ar), 7.10 (t, J=7.5 Hz, 1H, Ar), 7.19 (m, 1H, Ar), 7.27 (d, J=16.0 Hz, 1H, C=CH), 7.47 (d, J=8.0 Hz, 1H, Ar), 7.61 (d, J=7.5 Hz, 1H, Ar), 7.76 (d, J=7.5 Hz, 1H, Ar), 7.90 (d, J=16.0 Hz, 1H, C=CH), 9.90 (br s, 1H, OH).

Similarly prepared was:

Compound 3: (E)-2-[2-(Pyrazin-2-yl)vinyl]phenol

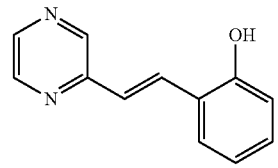 [SMILES: Oc1ccccc1/C=C/c1cnccn1]

From Intermediate 1; (E)-2-[2-(pyrazin-2-yl)vinyl]phenyl acetate (1.1 g, 4.5 mmol, 1.0 eq.) as an off-white solid (0.72 g, 81%); $^1$H NMR (400 MHz, DMSO-$d_6$) δ 6.82 (t, J=7.5 Hz, H, Ar), 6.88 (d, J=8.0 Hz, 1H, Ar), 7.19 (t, J=8.0 Hz, 1H, Ar), 7.32 (d, J=16.0 Hz, 1H, C=CH), 7.62 (t, J=7.5 Hz, 1H, Ar), 8.01 (d, J=16.0 Hz, 1H, C=CH), 8.45 (d, J=2.5 Hz, 1H, Ar), 8.61 (d, J=2.0 Hz, 1H, Ar), 8.74 (d, 1H, Ar), 10.01 (br s, 1H, OH).

Compound 4: (E)-2-[2-(Pyrazin-2-yl)vinyl]phenol hydrochloride

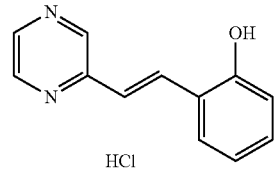 [SMILES: Oc1ccccc1/C=C/c1cnccn1 ; Cl]

From Compound 3; (E)-2-[2-(pyrazin-2-yl)vinyl]phenol (0.20 g, 1.01 mmol, 1.0 eq.) as a bright yellow solid (0.21 g, 82% yield); 1H NMR (400 MHz, DMSO-$d_6$) δ 6.85 (t, J=7.5 Hz, 1H, Ar), 6.93 (d, J=8.0 Hz, 1H, Ar), 7.17 (t, J=8.0 Hz, 1H, Ar), 7.36 (d, J=16.0 Hz, 1H, C=CH), 7.63 (d, J=7.5 Hz, 1H, Ar), 8.02 (d, J=16.0 Hz, 1H, C=CH), 8.46 (d, J=2.5 Hz, 1H, Ar), 8.60 (t, J=2.0 Hz, 1H, Ar), 8.73 (s, 1H, Ar), 10.01 (br s, 1H, OH).

Compound 5: (E)-2-[2-(Pyridin-4-yl)vinyl]phenol

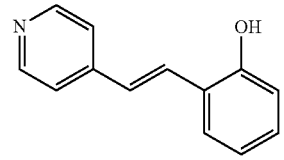

From Intermediate 6; (E)-2-[2-(pyridin-4-yl)vinyl]phenyl acetate (1.70 g, 7.0 mmol, 1.0 eq.) as an off-white solid (1.25 g, 63%); $^1$H NMR (400 MHz, DMSO-$d_6$) δ 6.84 (t, J=7.5 Hz, 1H, Ar), 6.90 (d, J=8.0 Hz, 1H, Ar), 7.16 (t, J=7.5 Hz, 1H, Ar), 7.21 (d, J=16.5 Hz, 1H, C=CH), 7.50 (d, J=6.0 Hz, 2H, Ar), 7.60 (d, J=8.0 Hz, 1H, Ar), 7.66 (d, J=16.5 Hz, 1H, C=CH), 8.51 (d, J=6.0 Hz, 2H, Ar), 9.92 (br s, 1H, OH).

Compound 6: (E)-2-[2-(Pyridin-4-yl)vinyl]phenol hydrochloride

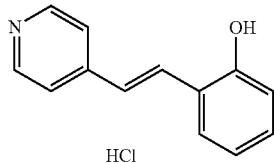 [SMILES: Oc1ccccc1/C=C/c1ccncc1 ; Cl]

From Compound 5; (E)-2-[2-(pyridin-4-yl)vinyl]phenol (100 mg, 0.47 mmol, 1.0 eq.) as bright yellow solid (89 mg, 78% yield); $^1$H NMR (400 MHz, DMSO-d$_6$) δ6.81 (t, J=7.5 Hz, 1H, Ar), 7.01 (d, J=8.0 Hz, 1H, Ar), 7.22 (t, J=7.5 Hz 1H, Ar), 7.39 (d, J=16.5 Hz 1H, C=CH), 7.62 (d, J=8.0 Hz, 1H, Ar), 7.89 (m, 3H, Ar & C=CH), 8.67 (d, J=6.0 Hz 2H, Ar), 10.31 (br s, 1H, OH).

Compound 7: (E)-2-[2-(6-Methylpyridin-2-yl)vinyl] phenol

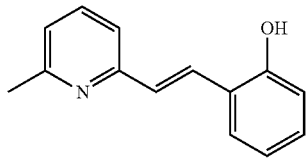 [SMILES: Cc1cccc(/C=C/c2ccccc2O)n1]

From Intermediate 8; (E)-2-[2-(6-methylpyridin-2-yl)vinyl]phenyl acetate (0.64 g, 2.5 mmol, 1.0 eq.) as an off-white solid (0.52 g, 98%); $^1$H NMR (400 MHz, DMSO-d$_6$) δ 2.49 (s, 3H, CH3), 6.82 (t, J=7.5 Hz, 1H, Ar), 6.89 (d, J=8.0 Hz, 1H, Ar), 7.08 (t, J=7.5 Hz, 1H, Ar), 7.12 (t, J=7.5 Hz, 1H, Ar), 7.22 (d, J=16.0 Hz, 1H, C=CH), 7.27 (d, J=8.0 Hz, 1H, Ar), 7.60 (d, J=7.5 Hz, 1H, Ar), 7.63 (t, J=7.5 Hz, 1H, Ar), 7.87 (d, J=16.0 Hz, 1H, C=CH), 9.83 (br s, 1H, OH).

Compound 8: (E)-2-[2-(6-Methylpyridin-2-yl)vinyl] phenol hydrochloride

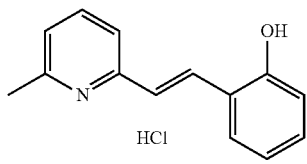 [SMILES: Cc1cccc(/C=C/c2ccccc2O)n1 ; Cl]

From Compound 7; (E)-2-[2-(6-methylpyridin-2-yl)vinyl]phenol as a bright yellow solid; $^1$H NMR (400 MHz, DMSO-d$_6$) δ2.50 (s, 3H, CH3), 6.85 (t, J=7.5 Hz, 1H, Ar), 6.98 (d, J=8.0 Hz 1H, Ar), 7.18 (t, J=7.5 Hz, 1H, Ar), 7.37 (d, J=8.0 Hz, 1H, Ar), 7.50 (d, J=16.0 Hz, 1H, C=CH), 7.59 (d, J=7.5 Hz, 1H, Ar), 7.77 (br s, 1H, Ar), 7.98 (d, J=16.0 Hz, 1H, C=CH), 8.00 (br s, 1H, Ar), 10.25 (br s, 1H, OH).

Compound 9: (E)-2-[2-(Pyridin-3-yl)vinyl]phenol

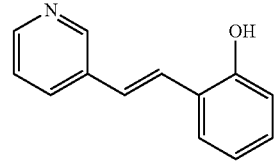

From Intermediate 7: (E)-2-[2-(pyridin-3-yl)vinyl]phenyl acetate as an orange solid; $^1$H NMR (400 MHz, DMSO-d$_6$) δ6.81 (t, J=7.5 Hz, 1H, Ar), 6.85 (d, J=8.0 Hz, 1H, Ar), 7.08 (t, J=7.5 Hz, 1H, Ar), 7.20 (d, 1H, J=16.0 Hz, C=CH), 7.35 (m, 1H, Ar), 7.49 (d, J=16.0 Hz, 1H, C=CH), 7.58 (d, J=7.5 1H, Ar), 7.99 (d, J=7.5, 1H, Ar), 8.45 (br s, 1H, Ar), 8.74 (br s, 1H, Ar), 9.80 (s, 1H, OH).

Compound 10: (E)-2-[2-(Pyridin-3-yl)vinyl]phenol hydrochloride

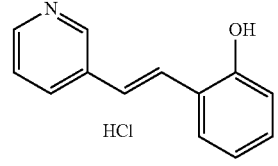 [SMILES: Oc1ccccc1/C=C/c1cccnc1 ; Cl]

From Compound 9: (E)-2-[2-(pyridin-3-yl)vinyl]phenol as a brown solid; $^1$H NMR (400 MHz, DMSO-d$_6$) δ6.81 (t, J=7.5 Hz, 1H, Ar), 6.87 (d, J=8.0 Hz, 1H, Ar), 7.14 (t, J=7.5 Hz, 1H, Ar), 7.27 (d, J=16.0 Hz, 1H, C=CH), 7.52-7.74 (m, 3H, Ar & C=CH), 8.31 (d, J=7.5 Hz, 1H, Ar), 8.59 (br s, 1H, Ar), 8.83 (br s, 1H, Ar), 10.00 (br s, 1H, OH).

Compound 11: (E)-2-[2-(Pyrazin-2-yl)prop-1-enyl] phenol

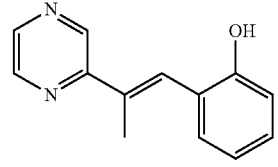 [SMILES: C/C(=C\c1ccccc1O)c1cnccn1]

From Intermediate 2; (E)-2-[2-(pyrazin-2-yl)prop-1-enyl] phenyl acetate as an off-white solid (0.26 g, 47% yield); $^1$H NMR (400 MHz, DMSO-d$_6$) δ 2.25 (s, 3H, CH3), 6.88 (t, J=7.5 Hz, 1H, Ar), 6.93 (d, J=7.5 Hz, 1H, Ar), 7.19 (t, J=7.5 Hz, 1H, Ar), 7.30 (d, J=7.5 Hz, 1H, Ar), 7.63 (s, 1H, C=CH), 8.54 (s, 1H, Ar), 8.65 (s, 1H, Ar), 8.95 (s, 1H, Ar), 9.68 (br s, 1H, OH).

Compound 12: (E)-2-[2-(Pyrazin-2-yl)prop-1-enyl]phenol hydrochloride

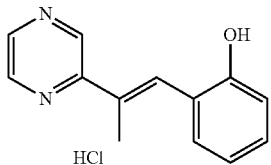 [SMILES: C/C(=C\c1ccccc1O)c1cnccn1 ; Cl]

From Compound 11; (E)-2-[2-(pyrazin-2-yl)prop-1-enyl]phenyl acetate (0.15 g, 0.71 mmol, 1.0 eq.) as a bright yellow solid; $^1$H NMR (400 MHz, DMSO-$d_6$) δ 2.25 (s, 3H, CH3), 6.85 (t, J=7.5 Hz, 1H, Ar), 6.91 (d, J=7.5 Hz, 1H, Ar), 7.15 (t, J=7.5 Hz, 1H, Ar), 7.30 (d, J=7.5 Hz, 1H, Ar), 7.61 (s, 1H, C=CH), 8.53 (s, 1H, Ar), 8.64 (s, 1H, Ar), 8.95 (s, 1H, Ar).

Compound 13: (E)-4-Methyl-[2-(2-(pyrazin-2-yl)vinyl)]phenol

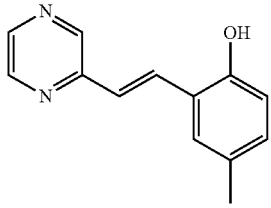 [SMILES: Cc1ccc(O)c(/C=C/c2cnccn2)c1]

From Intermediate 3; (E)-4-methyl-[2-(2-(pyrazin-2-yl)vinyl)]phenyl acetate (0.53 g, 2.1 mmol, 1.0 eq.) as a tan solid (0.40 g, 90% yield); $^1$H NMR (400 MHz, DMSO-$d_6$) δ 2.23 (s, 3H, CH3), 6.83 (d, J=8.0 Hz, 1H, Ar), 6.99 (d, J=8.0 Hz, 1H, Ar), 7.35 (d, J=16.0 Hz, 1H, C=CH), 7.45 (s, 1H, Ar), 8.00 (d, J=16.0 Hz, 1H, C=CH), 8.44 (s, 1H, Ar), 8.61 (s, 1H, Ar), 8.74 (s, 1H, Ar), 9.75 (s, 1H, OH).

Compound 14: (E)-4-Methyl-[2-(2-(Pyrazin-2-yl)vinyl)]phenol hydrochloride

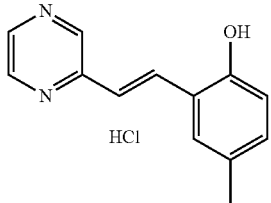 [SMILES: Cc1ccc(O)c(/C=C/c2cnccn2)c1 ; Cl]

From Compound 13; (E)-4-Methyl-[2-(2-(pyrazin-2-yl)vinyl)]phenol (0.20 g, 0.94 mmol, 1.0 eq.) as a yellow solid (0.21 g, 82% yield); $^1$H NMR (400 MHz, DMSO-$d_6$) δ 2.24 (s, 3H, CH3), 6.82 (d, J=8.0 Hz, 1H, Ar), 6.97 (d, J=8.0 Hz, 1H, Ar), 7.34 (d, J=16.0 Hz, 1H, C=CH), 7.45 (s, 1H, Ar), 8.00 (d, J=16.0 Hz, 1H, C=CH), 8.45 (s, 1H, Ar), 8.60 (s, 1H, Ar), 8.72 (s, 1H, Ar), 10.00 (vbr s, 1H, OH).

Compound 15: (E)-2-[2-(Pyrimidin-2-yl)vinyl]phenol hydrochloride

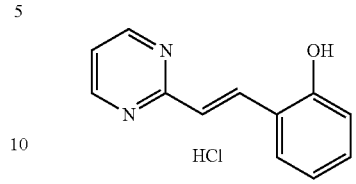

From Intermediate 4; (E)-2-[2-(pyrimidin-2-yl)vinyl]phenyl acetate (0.57 g, 2.4 mmol, 1.0 eq.), through (E)-2-(2-[pyrimidin-2-yl)vinyl]phenol (0.20 g, 1.1 mmol, 1.0 eq.) as a yellow solid (0.21 g, 81% yield); $^1$H NMR (400 MHz, DMSO-$d_6$) δ 6.85 (t, J=7.5 Hz, 1H, Ar), 6.95 (d, J=8.0 Hz, 1H, Ar), 7.20 (t, J=7.5 Hz, 1H, Ar), 7.32 (d, J=16.0 Hz, 1H, C=CH), 7.38 (t, J=5.0 Hz, 1H, Ar), 7.64 (d, J=16.0 Hz, 1H, C=CH), 8.26 (d, J=16.0 Hz, 1H, C=CH), 8.84 (d, J=5.0 Hz, 2H, Ar), 10.22 (br s, 1H, OH).

Procedure for the Preparation of Compound 16

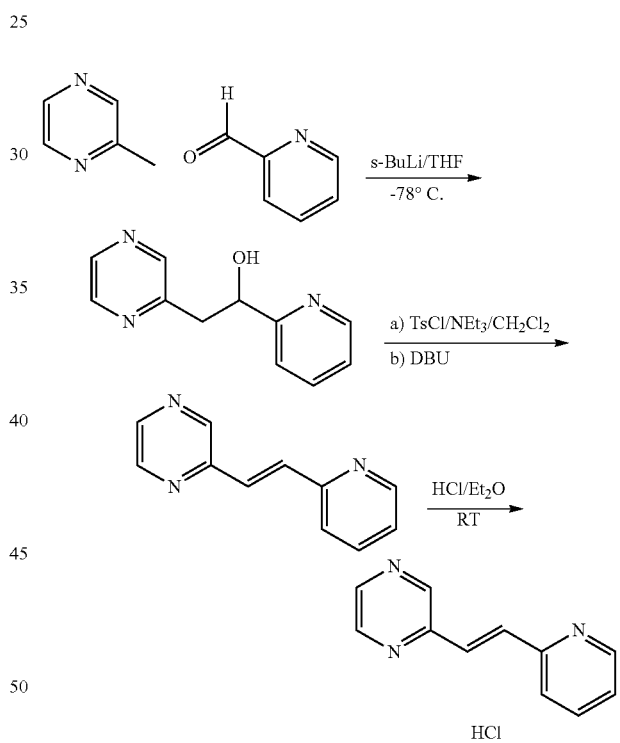

Compound 16: (E)-2-[2-(Pyridin-2-yl)vinyl]pyrazine hydrochloride

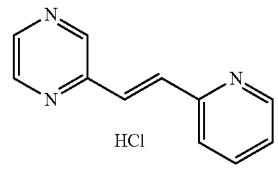 [SMILES: C(=C\c1cnccn1)/c1ccccn1 ; Cl]

s-Butyl lithium (2.5 M in hexanes, 4.8 mL, 12.0 mmol, 1.2 eq.) was added dropwise to a solution of diisopropylamine (1.83 mL, 1.32 g, 13.0 mmol, 1.3 eq.) in dry tetrahydrofuran (25 mL) at −78° C. The mixture was stirred at −78° C. for 10 min and 2-methylpyrazine (0.91 mL, 0.94 g, 10.0 mmol, 1.0 eq.) was added dropwise. The resulting mixture was stirred at −78° C. for a further 30 min 2-Pyridinecarboxaldehyde (0.96 mL, 1.07 g, 10.0 mmol, 1.0 eq.) was added dropwise and the mixture was allowed to slowly warm up to room temperature over 1 h while stirring. The reaction was quenched by addition of water (10 mL). The pH was adjusted to ~10 by careful addition of conc. HCl and then the mixture was extracted with dichloromethane (2×25 mL). The combined organic extracts were washed with brine (25 mL), dried over sodium sulfate and evaporated in vacuo. The crude product was purified by column chromatography (SiO$_2$, 1:9 methanol-ethyl acetate) to provide 2-(pyrazin-2-yl)-1-(pyridin-2-yl)ethanol (1.08 g, 54% yield) as a clear yellow oil.

p-Toluenesulfonyl chloride (1.12 g, 5.9 mmol, 1.1 eq.) was added to a stirred solution of 2-(pyrazin-2-yl)-1-(pyridin-2-yl)ethanol (1.08 g, 5.4 mmol, 1.0 eq.) and triethylamine (2.24 mL, 1.63 g, 16.1 mmol, 3.0 eq.) in dichloromethane (25 mL). The mixture was stirred at room temperature for 23 h. The mixture was washed with aqueous NaOH (15%, 25 mL), water (25 mL) and brine (25 mL). The organic layer was dried over sodium sulfate and evaporated in vacuo. The crude product was purified by column chromatography (SiO$_2$, 1:9 methanol-ethyl acetate) providing a mixture of 2-(pyrazin-2-yl)-1-(pyridin-2-yl)ethyl 4-methylbenzenesulfonate and (E)-2-(2-(pyridin-2-yl)vinyl)pyrazine (0.54 g).

1,8-Diazabicyclo[5.4.0]undec-7-ene (0.45 mL, 0.46 g, 3.0 mmol, 2.0 eq.) was added dropwise to a stirred solution of 2-(pyrazin-2-yl)-1-(pyridin-2-yl)ethyl 4-methylbenzenesulfonate (0.54 g, 1.5 mmol, 1.0 eq.) in dichloromethane (10 mL). The mixture was stirred at room temperature for 4 h. The mixture was evaporated in vacuo and the crude product was purified by column chromatography (SiO$_2$, ethyl acetate) providing (E)-2-(2-(pyridin-2-yl)vinyl)pyrazine (0.50 g, 100%) as a white solid.

A solution of hydrochloric acid (2.0 M in diethyl ether, 0.65 mL, 1.3 mmol, 1.2 eq.) was added dropwise to a stirred suspension of (E)-2-(2-(pyridin-2-yl)vinyl)pyrazine (0.20 g, 1.1 mmol, 1.0 eq.) in dry diethyl ether (7.5 mL). The mixture was stirred at room temperature for 1 h and then the solids removed by filtration. The product was washed with diethyl ether (3×10 mL) and then dried in vacuo to provide (E)-2-[2-(pyridin-2-yl)vinyl]pyrazine hydrochloride (0.21 g, 83% yield) as a fine white solid; $^1$H NMR (400 MHz, DMSO-d$_6$) δ 7.78 (t, J=7.0 Hz, 1H, Ar), 7.99 (d, J=16.0 Hz, 1H, C=CH), 8.11 (d, J=16.0 Hz, 1H, C=CH), 8.25 (d, J=8.0 Hz, 1H, Ar), 8.38 (t, J=8.0 Hz, 1H, Ar), 8.65 (d, J=2.5 Hz, 1H, Ar), 8.75 (t, J=2.0 Hz, 1H, Ar), 8.79 (d, J=5.0 Hz, 1H, Ar), 8.88 (d, J=2.0 Hz, 1H, Ar).

Procedure for the Preparation of Compound 17

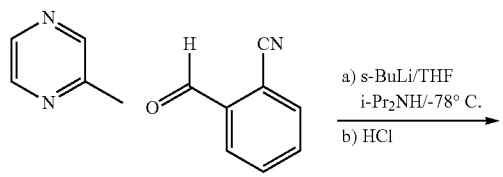

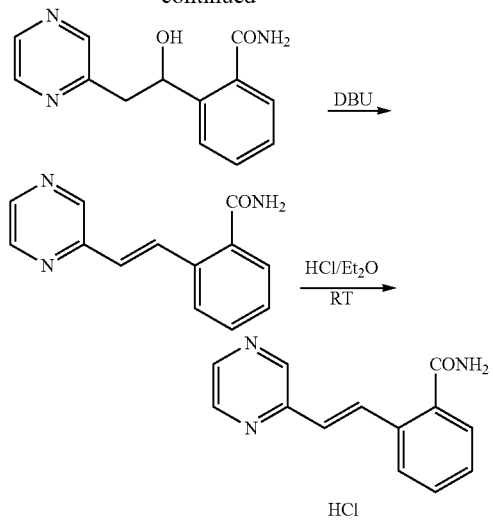

Compound 17: (E)-2-[2-(Pyrazin-2-yl)vinyl)benzamide hydrochloride

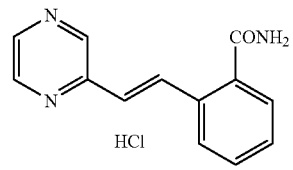 [SMILES: NC(=O)c1ccccc1/C=C/c1cnccn1 ; Cl]

n-Butyl lithium (2.5 M in hexanes, 4.8 mL, 12.0 mmol, 1.2 eq.) was added dropwise to a solution of diisopropylamine (1.83 mL, 1.32 g, 13.0 mmol, 1.3 eq.) in dry tetrahydrofuran (25 mL) at −78° C. The mixture was stirred at −78° C. for 10 min and 2-methylpyrazine (0.91 mL, 0.94 g, 10.0 mmol, 1.0 eq.) was added dropwise. The resulting mixture was stirred at −78° C. for 30 min. A solution of 2-cyanobenzaldehyde (1.31 g, 10.0 mmol, 1.0 eq.) in dry THF (10 mL) was added dropwise and the mixture was allowed to slowly warm up to room temperature over 2 h while stirring. The reaction was quenched by addition of water (20 mL). The pH was adjusted to ~10 by careful addition of conc. HCl and the mixture was extracted with dichloromethane (3×25 mL). The combined organic extracts were washed with brine (25 mL), dried over sodium sulfate and evaporated in vacuo. The crude product was purified by column chromatography (SiO$_2$, 1:9 methanol-ethyl acetate) providing 2-(1-hydroxy-2-(pyrazin-2-yl)ethyl)benzamide (1.06 g, 44% yield) as a clear yellow oil.

1,8-Diazabicyclo[5.4.0]undec-7-ene (1.61 mL, 1.69 g, 11.1 mmol, 2.5 eq.) was dropwise to a stirred solution of 2-[1-hydroxy-2-(pyrazin-2-yl)ethyl]benzamide (1.00 g, 4.4 mmol, 1.0 eq.) in dichloromethane (25 mL). The mixture was stirred at room temperature for 16 h. Water (25 mL) was added and the layers were separated. The aqueous layer was extracted with dichloromethane (2×25 mL) and the combined organic extracts washed with brine (25 mL), dried over sodium sulfate and concentrated in vacuo. The residue was taken up in ethyl acetate (20 mL) and filtered. The solids were washed with ethyl acetate (2×5 mL) and dried in vacuo providing (E)-2-[2-(pyrazin-2-yl)vinyl]benzamide (0.21 g, 21% yield) as a fine off-white solid.

A solution of hydrochloric acid (2.0 M in diethyl ether, 0.53 mL, 1.07 mmol, 1.2 eq.) was added dropwise to a stirred suspension of (E)-2-[2-(pyrazin-2-yl)vinyl]benzamide (0.20 g, 0.09 mmol, 1.0 eq.) in dry diethyl ether (7.5 mL). The mixture was stirred at room temperature for 1 h and was filtered. The solids were washed with diethyl ether (2×5 mL) and dried in vacuo providing (E)-2-[2-(pyrazin-2-yl)vinyl]benzamide hydrochloride (0.20 g, 86% yield) as a fine yellow solid; $^1$H NMR (400 MHz, DMSO-d$_6$) δ 7.33-7.55 (m, 5H, 2Ar+NH$_2$+C=CH), 7.88-7.96 (m, 2H, Ar), 8.11 (d, J=16.0 Hz, 1H, C=CH), 8.51 (s, 1H, Ar), 8.64 (s, 1H, Ar), 8.71 (s, 1H, Ar).

General Procedures for the Preparation of Compounds 18-23

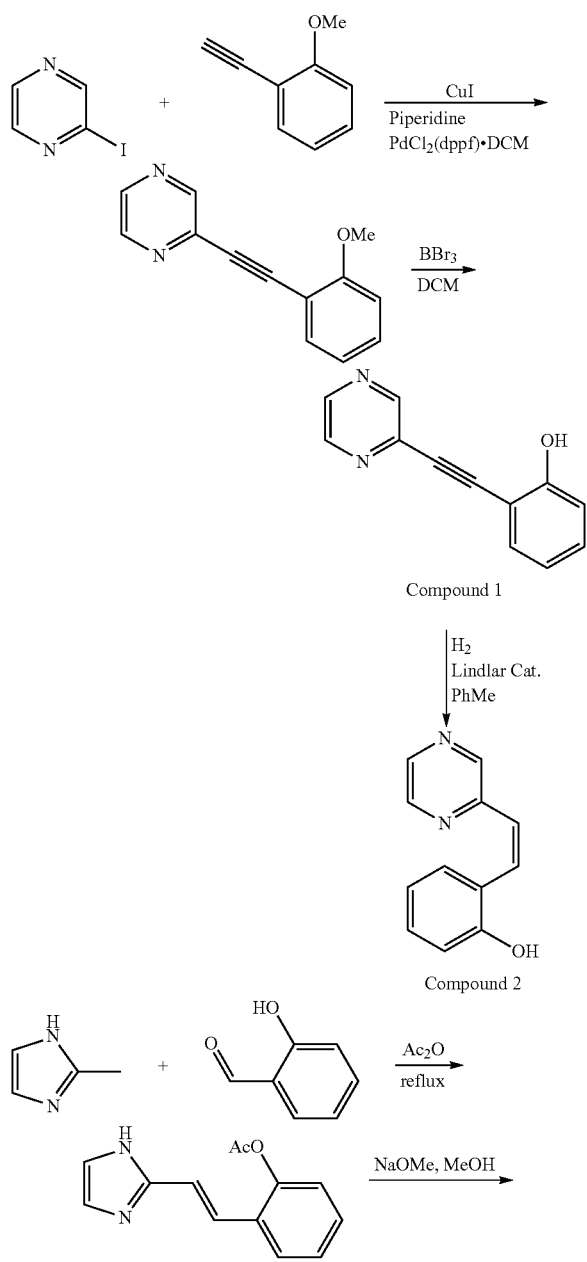

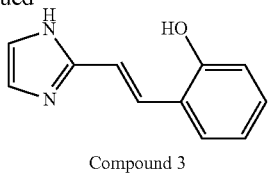

Compound 3

Compound 23: (E)-2-(2-(1H-Imidazol-2-yl)vinyl) phenol hydrochloride

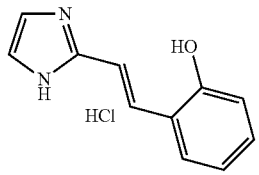 [SMILES: Oc1ccccc1/C=C/c1ncc[nH]1 ; Cl]

(E)-2-[2-(1H-imidazol-2-yl)vinyl]phenyl acetate [Intermediate 9; (440 mg, 1.93 mmol)] was dissolved in methanol (8 ml) and placed under a nitrogen atmosphere. The solution was treated with sodium methoxide (10 mg, 0.193 mmol) and stirred at room temperature for 2 h. The reaction was concentrated in vacuo providing the crude product as an orange solid (265 mg). The crude product was purified by chromatography (5-10% MeOH: DCM). The combined fractions were concentrated in vacuo providing 186 mg of product (Compound 22—free base) with a purity of 99.7% by LC and >95% by $^1$H NMR. 110 mg of the free base was dissolved in 1:1 MeOH: DCM (5 ml) and treated with 2M HCl in diethyl ether (0.3 ml, 0.6 mmol). The solution was concentrated in vacuo providing 120 mg of (E)-2-(2-(1H-imidazol-2-yl)vinyl)phenol hydrochloride as an orange foam with a purity by LC of 99.3%, $^1$H NMR (270 MHz, DMSO-d$_6$) δ6.81-6.88 (2H, m), 7.02-7.09 (4H, m, Ar+C=CH), 7.44-7.52 (2H, m, Ar+C=CH), 9.91 (1H, s, NH).

Compound 19:
2-[2-(2-Methoxyphenyl)ethynyl]pyrazine

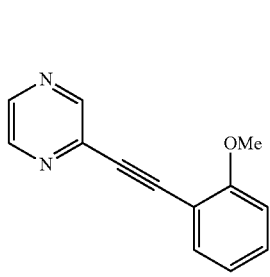 [SMILES: COc1ccccc1C#Cc1cnccn1]

2-Iodopyrazine (4.7 g, 22.85 mmol) and ethnylanisole (3.02 g, 22.85 mmol) were combined in THF (470 mL) and piperidine (4.06 mL, 41.1 mmol). The solution was then vacuum degassed three times releasing to Na. CuI (87 mg, 0.46 mmol) and PdCl$_2$(dppf).DCM (373 mg, 0.46 mmol) were added and the resulting mixture stirred at ambient temperature for 72 hours. The reaction mixture was then concentrated in vacuo and the residue partitioned between EtOAc (50 mL) and 10% aqueous citric acid (25 mL). The phases were separated and the aqueous extracted further with EtOAc (50 mL). The combined organics were concentrated to give 6.4 g of a black oil. This was purified by chromatography [1:4 EtOAc:Heptane] to give 4.04 g of 2-(2-(2-methoxyphenyl)ethynyl)pyrazine (84% yield, 93% purity by LCMS); $^1$H NMR (270 MHz, CDCl$_3$) δ 3.92 (s, 3H), 6.94 (m, 2H), 7.37 (m, 1H), 7.56 (dd, 1H, J=7.3 Hz, 1.6 Hz), 8.46 (d, 1H, J=2.7 Hz), 8.57 (t, 1H, J=2.2 Hz), 8.77 (d, 1H, J=1.6 Hz).

Compound 18: 2-[2-(Pyrazin-2-yl)ethynyl]phenol

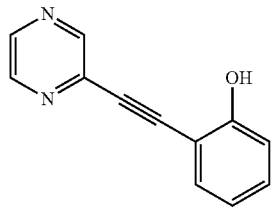 [SMILES: Oc1ccccc1C#Cc1cnccn1]

To a solution of 2-[2-(2-methoxyphenyl)ethynyl]pyrazine [Compound 19; (1.046 g, 4.98 mmol)] in DCM (230 mL) was added a 1M solution of BBr$_3$ in DCM (24.9 mL, 24.9 mmol) maintaining the temperature<0° C. The resulting solution was stirred for 1 hour at −10-0° C., before allowing to warm to room temperature and stirring for 18 hours. The reaction was quenched with 0.1 M NaOH (650 mL) maintaining temperature <20° C. to give pH of 9-10. The phases were then separated and the organics extracted twice with 0.5M NaOH. The combined aqueous phases were adjusted to pH 6 with HCl, extracted with EtOAc and the organics dried over MgSO$_4$, filtered and concentrated in vacuo to provide 2-[2-(pyrazin-2-yl)ethynyl]phenol (927 mg, 95%) as a yellow solid; $^1$H NMR (270 MHz, DMSO-d$_6$) δ 6.87 (td, 1H, J=7.6 Hz, 1.1 Hz), 6.97 (d, 1H, J=7.6 Hz), 7.31 (m, 1H), 7.47 (dd, 1H, 7.8 Hz, 1.9 Hz), 8.62 (d, 1H, J=2.7 Hz), 8.68 (m, 1H), 8.83 (d, 1H, J=1.4 Hz), 10.32 (1H, s, OH).

Compound 20: 2-[2-(pyrazin-2-yl)ethynyl]phenol hydrochloride

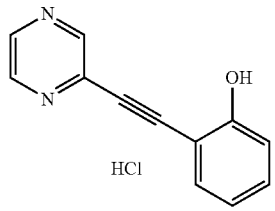

2-[2-(Pyrazin-2-yl)ethynyl]phenol [Compound 19; (150 mg, 0.765 mmol) was slurried in 2M HCl in Et$_2$O (5 mL) for 1 hour. The reaction was then concentrated in vacuo to give 2-(2-(pyrazin-2-yl)ethynyl)phenol hydrochloride as a bright yellow solid (130 mg, 72% yield); $^1$H NMR (270 MHz, DMSO-d$_6$) δ 6.87 (td, 1H, J=7.6 Hz, 1.1 Hz), 6.97 (d, 1H, J=7.6 Hz), 7.31 (m, 1H), 7.47 (dd, 1H, 7.8 Hz, 1.9 Hz), 8.62 (d, 1H, J=2.7 Hz), 8.68 (m, 1H), 8.83 (d, 1H, J=1.4 Hz), 10.32 (1H, s, OH).

Compound 21: (Z)-2-[2-(Pyrazin-2-yl)vinyl]phenol

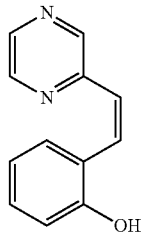

2-[2-(Pyrazin-2-yl)ethynyl]phenol [Compound 20; (284 mg, 1.45 mmol)] was dissolved in toluene (20 ml) and Lindlar's catalyst (30 mg, 10 mol %) was added to the solution. The reaction was purged with nitrogen (×3) and hydrogen (×3) and placed under 5 bar hydrogen pressure. The mixture was heated to 45° C. (oil bath temperature). After 4 h there was 15% product and the reaction was left under a nitrogen atmosphere over the weekend. Additional catalyst (30 mg, mol %) was added to the reaction which was heated to 45° C. and pressurized to 5 bar hydrogen. After leaving overnight the level of product had increased to 40%. As the reaction was slowing down it was filtered through Celite and Lindlar's catalyst (60 mg, 20 mol %) was added to the yellow solution. The reaction solution was charged to the vessel and heated to 45° C. and pressurised to 5 bar hydrogen and stirred overnight. The following morning starting material had been consumed but the trans isomer and the over reduced alkane had formed. The reaction was filtered through Celite and the filtrate was concentrated in vacuo producing a brown oil. The crude product was purified by chromatography (2% MeOH: DCM). The product containing fractions were combined and concentrated in vacuo providing 168 mg of material containing; product (51.9%), trans isomer (17.2%) and over reduced product (17.3%). The compounds co-ran by TLC and the material was submitted for prep LC. The aqueous LC fractions were neutralised with solid NaHCO$_3$ and extracted with 5% MeOH: DCM (2×10 ml). The organics were dried over MgSO$_4$, filtered and concentrated in vacuo providing 33 mg of the desired product with a purity of 82% by LC and containing 9.2% alkane and 8.34% of the trans isomer. $^1$H NMR (270 MHz, DMSO-d$_6$) δ 6.59-6.68 (2H, m), 6.87 (1H, d, J=10.8 Hz), 6.96-7.03 (1H, m), 7.12 (1H, m), 8.34 (1H, d, J=1.4 Hz), 8.38 (1H, d, J=2.4 Hz), 8.55 (2H, m), 9.73 (1H, s, OH).

We have identified small molecule compounds that exhibit an anti-angiogenic effect, in vivo. The anti-angiogenic compounds may be used to treat inappropriate blood vessel formation (neovascularisation) such as the neovascularisation associated with debilitating forms of human blindness, including age-related macular degeneration (AMD) and diabetic retinopathy (DR). Additionally, these compounds may have therapeutic benefits in cancer, by cutting off the blood supply to tumours or by inhibiting the secretion of angiogenic and/or inflammatory factors from a tumour.

The compound may be administered to patients with diseases characterised by neovascularisation such as forms of progressive blindness that would benefit from stunting the growth of inappropriate new blood vessels, or cancer patients in which tumour growth can be halted by cutting off blood supply or by inhibiting the secretion of angiogenic and/or inflammatory factors from the tumour.

The anti-angiogenic compounds described herein have the potential to offer patients effective, easily administered, safe and cost-effective treatments to prevent vision loss and tumour growth The compounds described herein effectively inhibit new vessel growth. In the case of anti-angiogenic treatments for the eye, the compounds have the potential to be administered in the conventional manner as an injection or as eye drops as their small chemical size facilitates absorption from the cornea, unlike antibodies which require intravitreal injection. Similar-sized small molecules have been shown to exhibit anti-angiogenic efficacy in the eye upon topical administration (Doukas et al., 2008).

Topical administration of the compound, such as through eye drops, will eliminate the repeated injections that are required for the administration VEGF antibodies will reduce the safety risks associated with repeated intravitreal injections. Furthermore, small molecule compounds will be cheaper to manufacture than antibodies and unlike antibodies, no potentially hazardous biological components are required to synthesise the compounds which will reduce the manufacturing costs and regulatory safety requirements.

We have used the zebrafish model as an in vivo screen of chemical compounds as the small size and transparency of the zebrafish enables high-content screens in multi-well plate formats (MacRae and Peterson, 2003; Pichler et al., 2003; Peterson et al., 2004; den Hertog, 2005; Zon and Peterson, 2005). Furthermore, many drugs have been shown to have comparable actions in humans and zebrafish including aspirin, warfarin, L-NAME, carbachol and diazepam (Goldsmith, 2004). To identify anti-angiogenic compounds we used a transgenic line of zebrafish that expresses a fluorescent reporter (EGFP) specifically in vasculature (Tg (fli1:efgp)). This line was obtained from the Zebrafish International Resource Center. Our assay involved screening the effect of compounds on the development of blood vessels in zebrafish. Specifically, we looked at the integrity of vessels developing in the eye (hyaloid vessels attached to the lens) and in the trunk. From these screens we have identified compounds that exhibited reproducible anti-angiogenic activity in vivo. Our characterisation of compounds was based on significant inhibition of hyaloid vessel formation in terms of pattern or primary branch number.

Compounds Tested

The following compounds were screened in the zebrafish model as described in Examples 1 and 2 below.

Figure 1B:
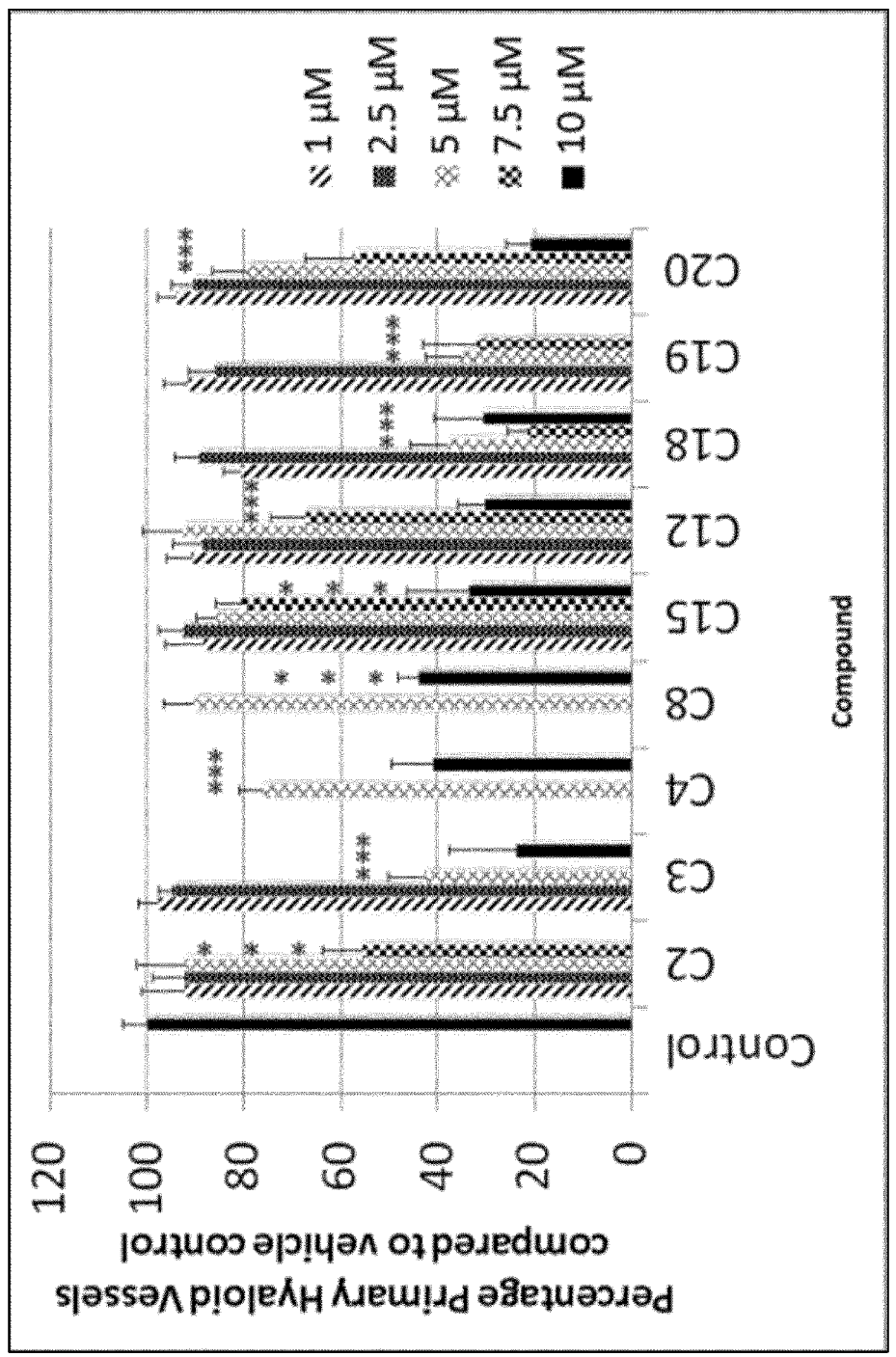
FIG. 1B is a graph showing the effect of a range of concentrations 1, 2.5, 5, 7.5 and 10 µM of tested compounds on inhibiting developmental angiogenesis of the primary hyaloid vessels in zebrafish. n>=8, ***p-value≤0.001. Data shown is mean+SEM and expressed as a percentage of the vehicle control.
Figure 2:
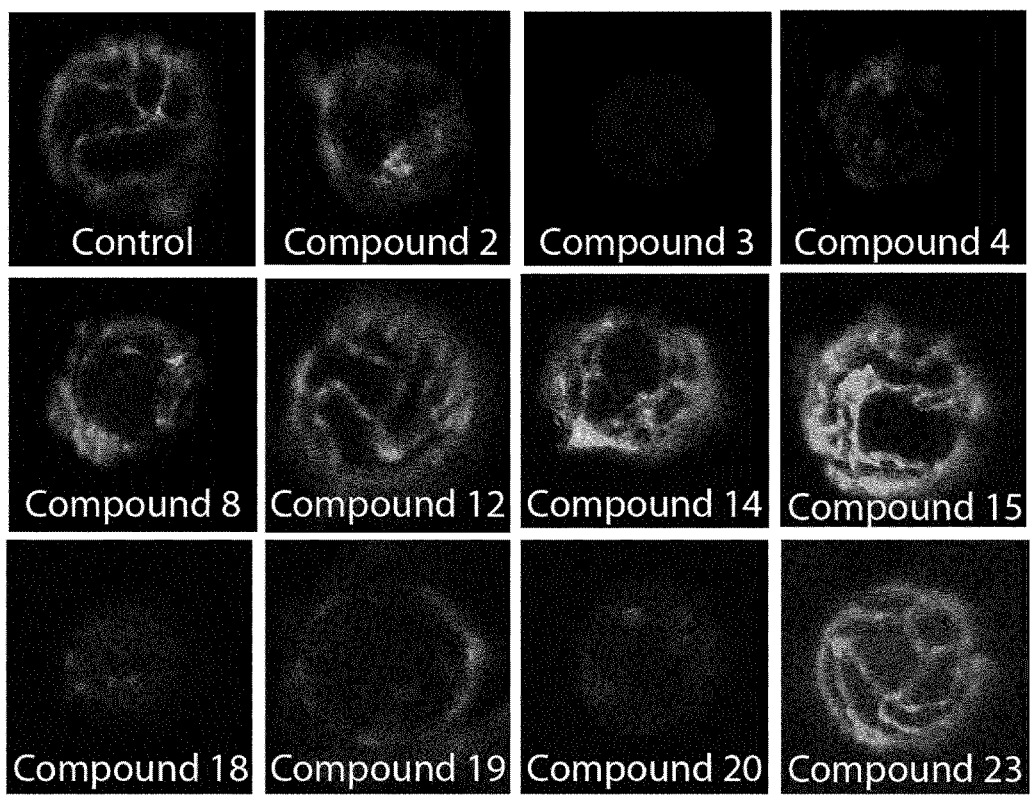
FIG. 2 are representative images showing the effect of 10 µM of tested compounds on inhibiting developmental angiogenesis of the primary hyaloid vessels in zebrafish.

Example 1—Quantification of Primary Hyaloid Vasculature Branch Number. (FIG. 1A, FIG. 1B and FIG. 2)

All experiments were carried out under ethical approval granted by the UCD animal research ethics committee. Tg(fli1:EGFP) zebrafish were maintained according to standard procedures on a 14 hr light/10 hr dark cycle at 28° C. Embryos were obtained by natural spawning and developmental stages established by time and morphological criteria. At 48 hours post fertilisation (hpf), 5 embryos per well were placed in 400 μl of Embryo Medium/0.1% DMSO and incubated with compound (typically, 10 μM) at 28° C. on a 14 h light/10 h dark cycle. At 5 days post fertilisation (dpf), larvae were euthanised, and fixed in 4% PFA at 4° C. overnight before analysis.

Prior to analysis of the intraocular vasculature, the control and treated larvae were observed under an Olympus SZX16 stereo zoom microscope and screened for general malformations. Overall patterning of the vasculature (fin, gut and intersegmental vessels) was examined for abnormalities. Right lenses were dissected from the larvae and transferred to depression slides for observation under epi-fluorescence in the Olympus SZX16. Patterning of the hyaloid vessels on the treated larval lenses was compared to 0.1% DMSO controls and the archetypal pattern previously described (Alvarez et al., 2007; Alvarez et al., 2009). The number of primary vessels radiating from the back of the lens (3-4 main branches at 5 dpf in controls and previously described), was counted and the average number was graphed for each drug. Compounds 20, 3, 12, 18, 15, 4, 8, 11, 14, 1, 2, 13 and 23 inhibit developmental angiogenesis of the zebrafish hyaloid vasculature in a statistically significant manner at 10 μM drug concentration. Compounds 2, 3, 4, 8, 12, 18, 19 and 20 inhibit developmental angiogenesis of the zebrafish hyaloid vasculature in a statistically significant manner at concentrations below 10 μM.

Figure 3:
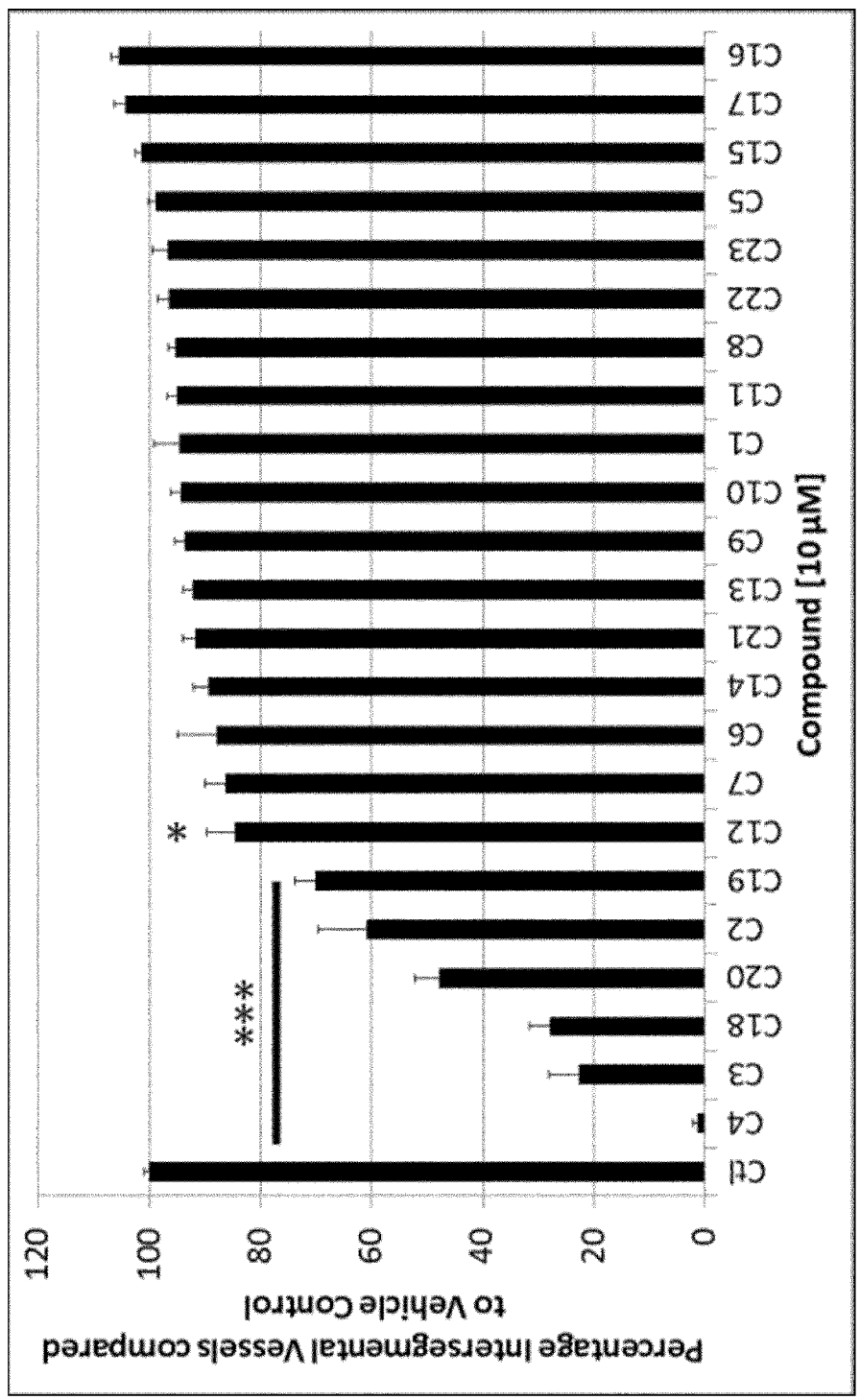
FIG. 3 is a graph showing the effect of 10 µM of tested compounds on inhibiting developmental angiogenesis of the intersegmental vasculature in zebrafish. n>=12, ***p-value≤0.001, *p-value≤0.05. Data shown is mean+SEM and expressed as a percentage of the vehicle control.
Figure 4:
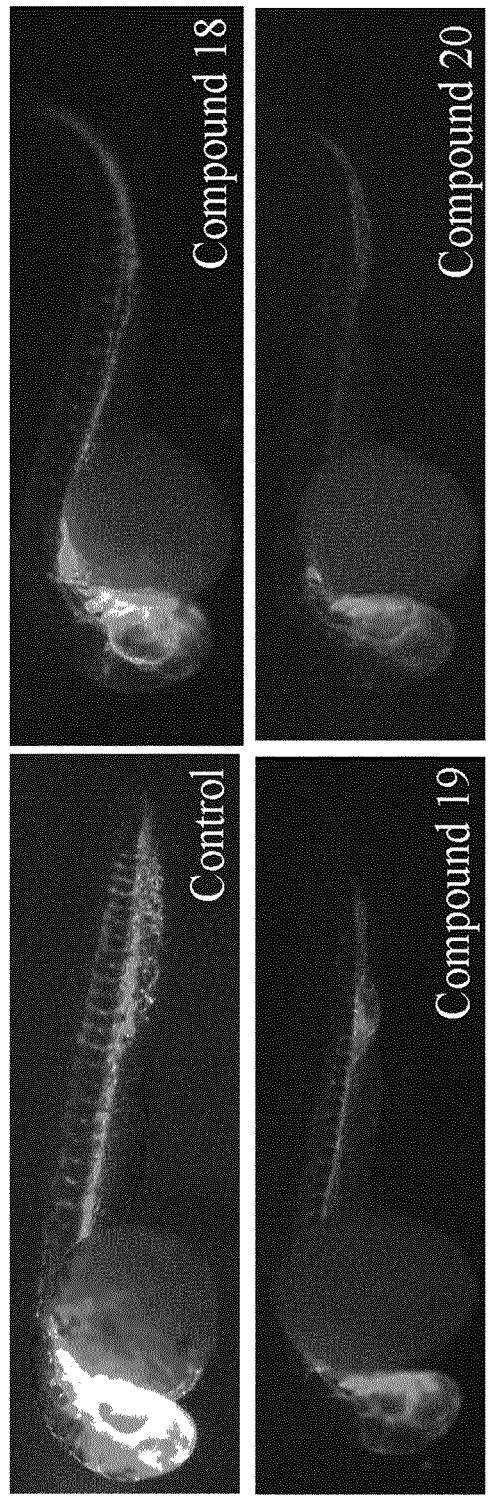
FIG. 4 are representative images showing the effect of 10 µM of tested compounds on inhibiting developmental angiogenesis of the intersegmental vasculature in zebrafish.

Example 2—Quantification of Intersegmental Vessel Number. (FIG. 3 and FIG. 4)

At 6 hours post fertilisation, 5 embryos per well were placed in 400 μL of embryo medium/0.1% DMSO and incubated with 10 μM compound at 28° C. on a 14 h light/10 h dark cycle. At 48 hpf larvae were manually dechorionated, euthanised, and fixed in 4% PFA at 4° C. overnight before analysis. The larvae were then washed with PBS and transferred to depression slides for observation under epi-fluorescence in an Olympus SZX16 fluorescent microscope. The number of intersegmental vessels was counted and the average number was graphed for each drug. Compounds 4, 3, 18, 20, 2, 19 and 12 inhibit developmental angiogenesis of zebrafish intersegmental vessels in a statistically significant manner.

Figure 5:
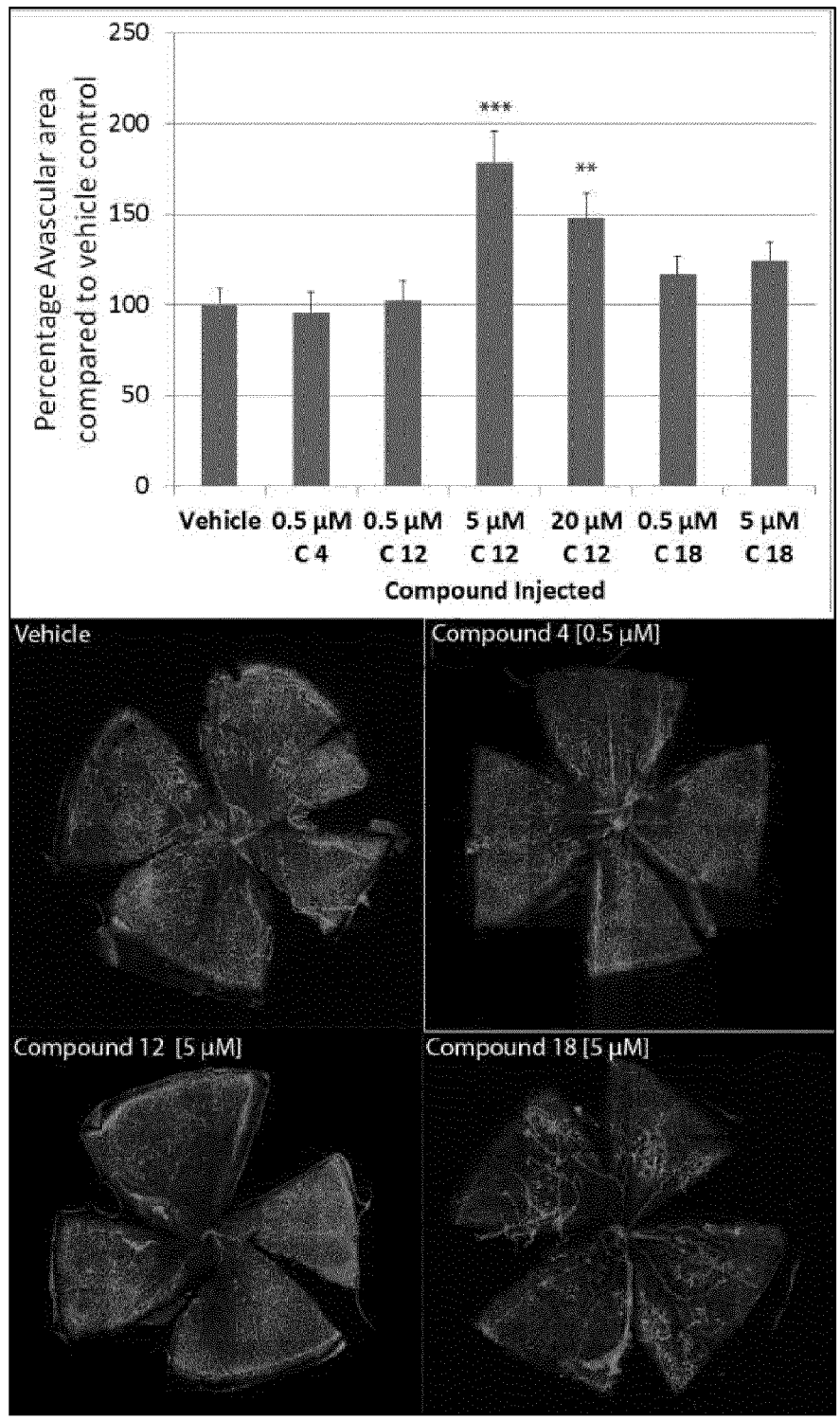
FIG. 5 is a graph (top) and representative isolectin-stained, flat-mounted retina images (bottom) showing the effect of 0.5, 5, 10 or 20 µM of compounds 4, 12 and 18 or vehicle control on inhibiting retinal neovascularisation in the oxygen induced mouse model of retinopathy. Compound 12 significantly reduces retinal neovascularisation in this model at 5 and 20 µM. n>=7, *p-value≤0.001, p-value≤0.01. Data shown is mean+SEM and expressed as a percentage of the vehicle control.

Example 3—Quantification of Anti-Angiogenic Activity in a Mouse Model of Neovascularisation (Oxygen-Induced Retinopathy Model). (FIG. 5)

The mouse oxygen-induced retinopathy model was used to test the anti-angiogenic activity of compounds 4, 12 and 18. Mouse pups (together with their dams) were placed in 75% oxygen from postnatal day (P) 7 to P12, causing a regression of their retinal blood vessels. On P12, pups were placed back in normoxia (21%) causing a regrowth of retinal blood vessels. Pups received an intravitreal injection on P12, of compound 4, 12, 18 or vehicle control—Hank's Balanced Salt Solution, coinciding with their return to normoxia. Pups were culled on P17 and enucleated. Eyes were fixed in 4% paraformaldehyde, washed and dissected to form retinal flatmounts. Flatmounts were stained with isolectin to visualise blood vessels and imaged. The central avascular area (lacking a network of blood vessels) was quantified using FIJI image analysis software. Compound 12 inhibits retinal revascularisation in a statistically significant manner at 5 and 20 μM.

Figure 6:
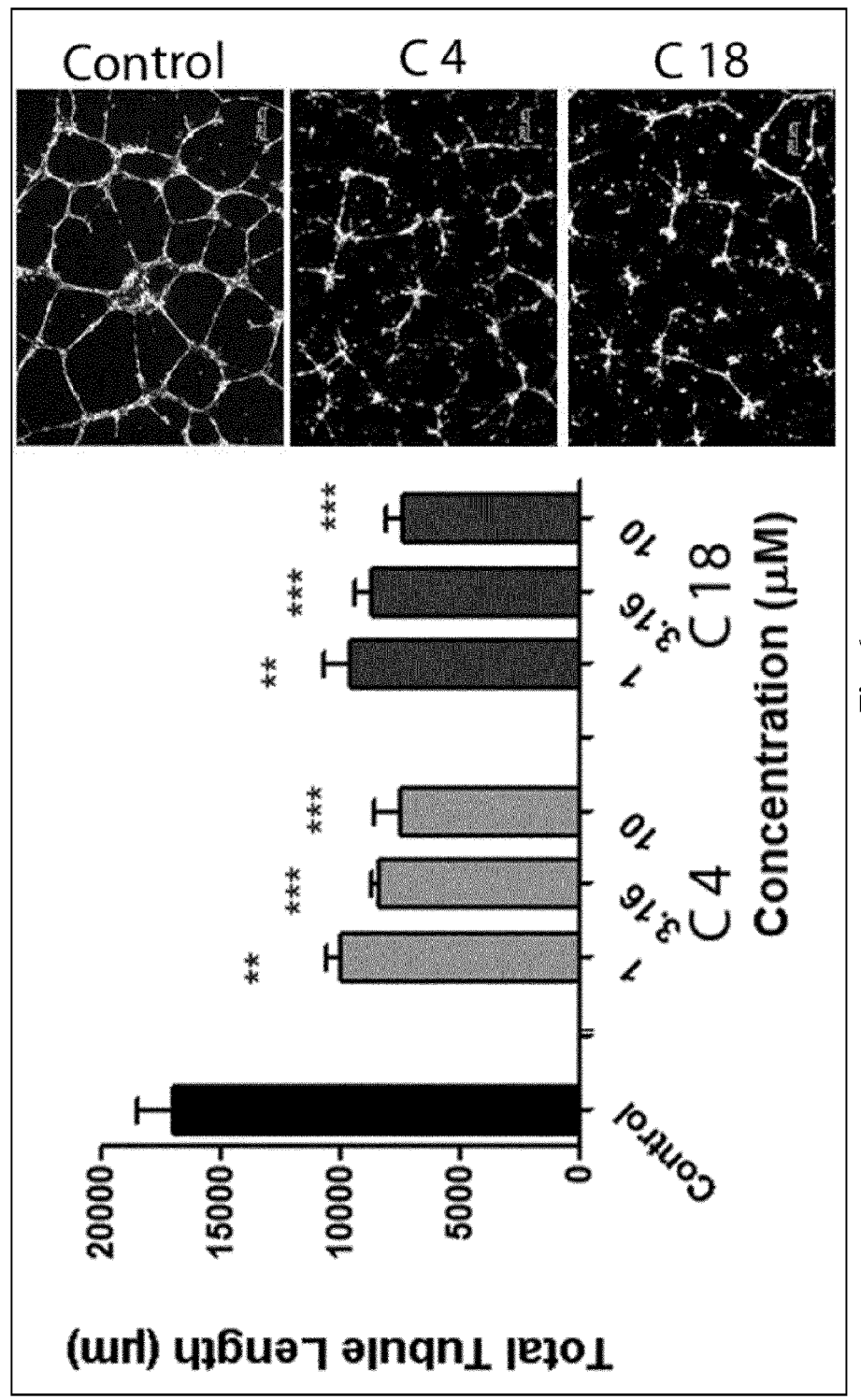
FIG. 6 is a graph (left) and representative fluorescent (calcein stained) images (right) showing the effect of 1, 3.16 or 10 µM of compound 4, 18 or vehicle control on inhibiting tubule formation in human microvascular endothelial cells (HMECs). Compound 4 and 18 significantly reduce tubule formation at all concentrations tested. N=3, *p-value≤0.001, p-value≤0.01. Data shown is mean+SEM.

Example 4—Quantification of In Vitro Tubule Formation in Human Microvascular Endothelial Cells. (FIG. 6)

Dermal-derived Human Microvascular Endothelial Cells (HMEC) were maintained at 37° C./5% CO2 in MCDB-131 medium (Gibco/cat: 10372) supplemented with 10% FCS, L-Glutamine (Gibco/cat: 25030-032), 1 μl/ml Hydrocortisone (Sigma/cat: H0396), 10 ng/ml EGF (BD Biosciences 354001) and 1% Pen-Strep (Gibco/cat: 151040-148). The wells of a μ-slide angiogenesis plate (IBIDI Cat no: 81506) were coated with a layer of matrigel matrix (BD 356234) which was left to polymerize for 45 minutes at 37° C. HMECs were grown to 80% confluence, washed with DPBS (Invitrogen) and trypsinised using 2 ml TrypLE™ Express (1×) (Invitrogen). Cells were centrifuged following flask detachment at 1200 rpm for 4 minutes. The cell pellet was resuspended in 3 ml full media and a cell count was performed using a haemocytometer. $7.5×10^3$ cells were pipetted into each matrigel coated well of the μ-slide angiogenesis plate and treated with either 0.1% DMSO or 1, 3.16 or 10 μM compound 4 or compound 18. The slide was kept at 37° C./5% CO2 during cell tube formation. After 16 hours, the cells were imaged by phase contrast microscopy using the Zeiss Axiovert 200 M microscope. Total tubule length was quantified using Zeiss Axiovision image analysis software. Calcein AM stain (C3099 Invitrogen) was prepared at 2 μg/ml final concentration and incubated with HMEC cells following tubule formation for 30 minutes at 37° C. Cells were imaged using fluorescent microscopy. Compounds 4 and 18 inhibit in vitro tubule formation in a statistically significant manner at 1, 3.16 and 10 μM.

Figure 7:
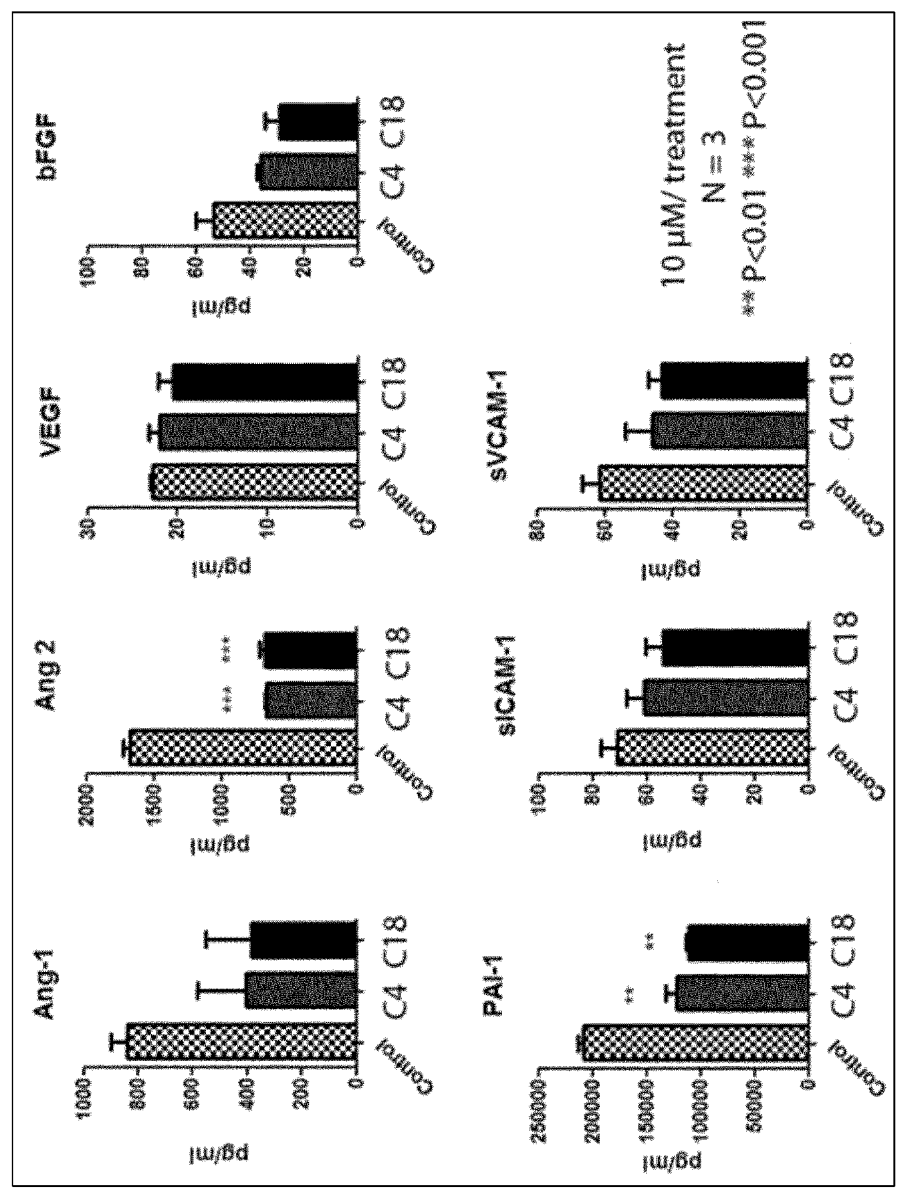
FIG. 7 is a set of graphs showing that compound 4 and 18 significantly reduce the expression of Ang-2 and PAI-1 in compound-treated HMECs. The expression of Ang-1, VEGF, bFGF, sICAM-1 and sVCAM-1 were not significantly different to control-treated HMECs. N=3, *p-value≤0.001, p-value≤0.01. Data shown is mean+SEM.

Example 5—Compound 4 and 18 Significantly Reduce Expression of Ang-2 and PAI-1 in Human Microvascular Endothelial Cells (HMECs) In Vitro. (FIG. 7)

Dermal-derived Human Microvascular Endothelial Cells (HMEC) were maintained at 37° C./5% CO2 in MCDB-131 medium (Gibco/cat: 10372) supplemented with 10% FCS, L-Glutamine (Gibco/cat: 25030-032), 1 μl/ml Hydrocortisone (Sigma/cat: H0396), 10 ng/ml EGF (BD Biosciences 354001) and 1% Pen-Strep (Gibco/cat: 151040-148). The wells of a μ-slide angiogenesis plate (IBIDI Cat no: 81506) were coated with a layer of matrigel matrix (BD 356234) which was left to polymerize for 45 minutes at 37° C. HMECs were grown to 80% confluence, washed with DPBS (Invitrogen) and trypsinised using 2 ml TrypLE™ Express (1×) (Invitrogen). Cells were centrifuged following flask detachment at 1200 rpm for 4 minutes. The cell pellet was resuspended in 3 ml full media and a cell count was performed using a haemocytometer. $7.5×10^3$ cells were pipetted into each matrigel coated well of the μ-slide angiogenesis plate and treated with either 0.1% DMSO or 1, 3.16 or 10 μM compound 4 or compound 18. The slide was kept at 37° C./5% CO2 during cell tube formation. After 16 hours, 50 μl of media was removed from each of the Ibidi wells and 25 μl of the media was run in each well of a Meso Scale Discovery (MD, USA) custom multiplex ELISA containing the following analytes: Ang-1, Ang-2, VEGF, bFGF, PAI-1, sICAM and sVCAM. The ELISA was run as per manufacturer's instructions. Compounds 4 and 18 reduce expression of Ang-2 and PAI-1 in human endothelial microvascular cells in a statistically significant manner.

Figure 8A:
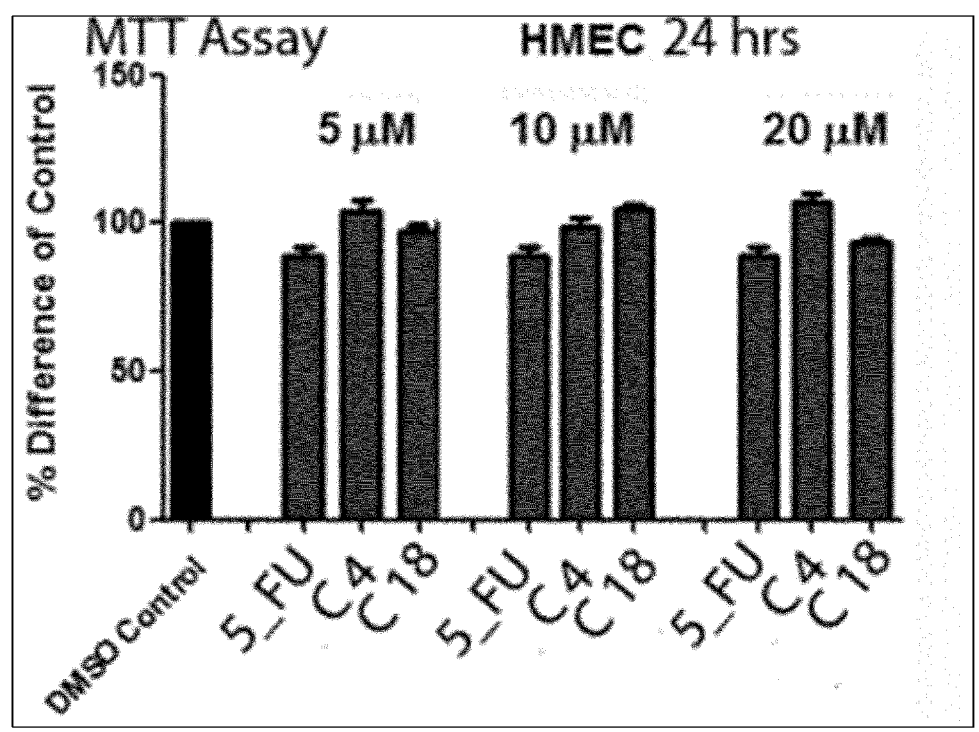
FIG. 8A is a graph showing that treatment with 10 µM compound 4, or 18 does not affect cell viability at 24 hours in human endothelial (HMEC) cells. Graph depicts results from drug-treating cells and performing the MTT assay N=3. Data shown is normalised to control and graphed as mean+SEM.
Figure 8B:
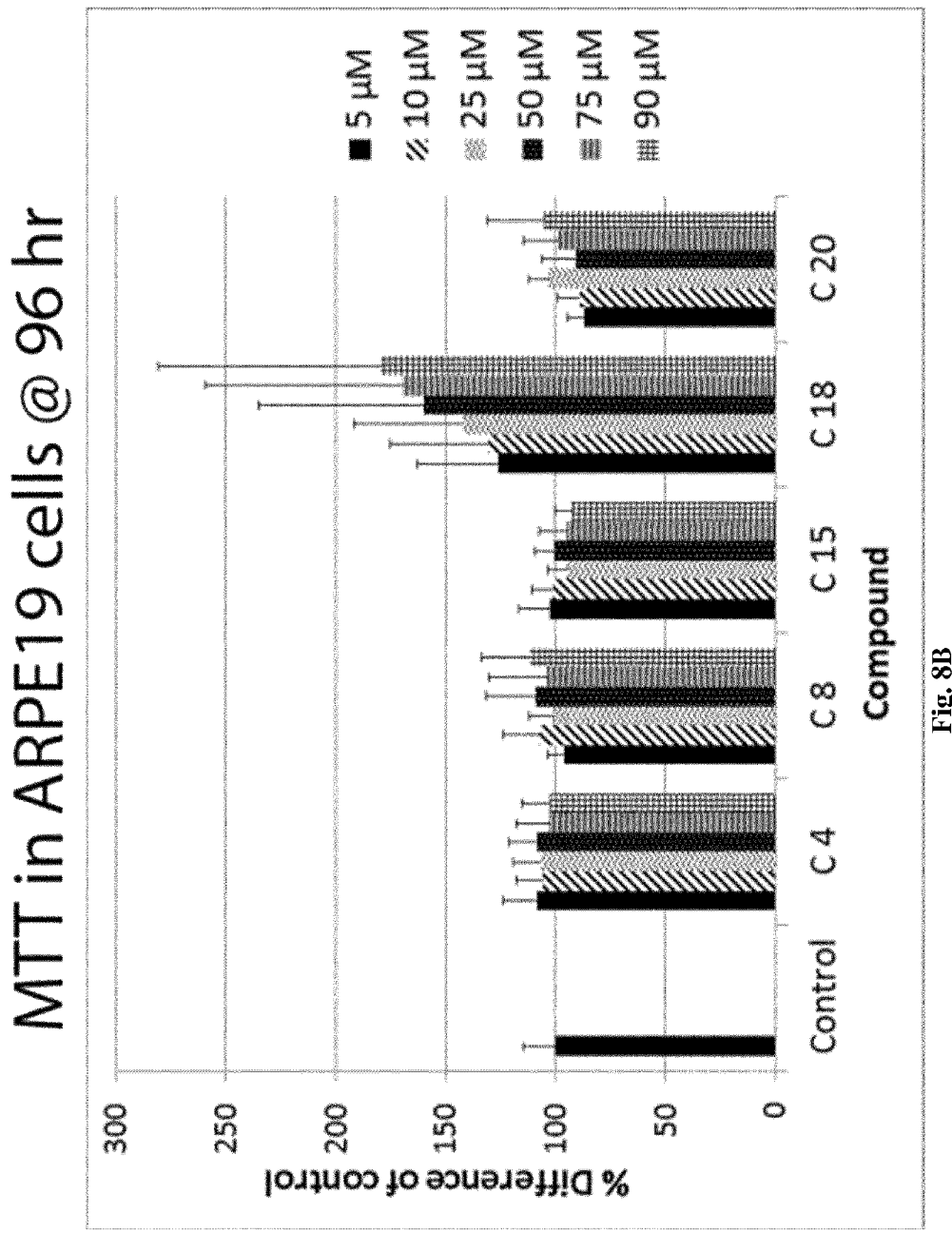
FIG. 8B is a graph showing that treatment with 5, 10, 25, 50, 75 or 90 µM compound 4, 8, 15, 18 or 20 does not affect cell viability at 96 hours in human retinal (ARPE-19) cells. Graph depicts results from drug-treating cells and performing the MTT assay in (A) human retinal ARPE-19 cells. N=3, Data shown is normalised to control and graphed as mean+SEM.

Example 6—Quantification of Cell Viability in Endothelial and Retinal Cells Using 3-(4,5-Dimethylthiozol-2-Yl)-2,5-Diphenyltetrazolium Bromide (MTT) Dye Reduction Assay. (FIG. 8A and FIG. 8B)

A 3-(4,5-dimethylthiozol-2-yl)-2,5-diphenyltetrazolium bromide (MTT) dye reduction assay was carried out to determine the cytotoxicity of each compound on either human microvascular endothelial cells (HMECs) or human retinal pigmented epithelium cells (ARPE-19). Cells were maintained in a 95% air and 5% CO2 atmosphere at 37° C. in Dulbecco modified Eagle medium (DMEM, Sigma Aldrich) with 10% fetal bovine serum, 2 mM Gibco® L-glutamine and 100 units/ml penicillin, 1 mg/ml streptomycin (Invitrogen) supplementation. On day 1, cells were trypsinized (Trypsin-EDTA 1×) and seeded $1.4×10^4$ cells per well of a 96 well plate and incubated overnight. On day 2, cells were serum staved in DMEM with L-glutamine and penicillin-streptomycin supplementation for 24 h. On day 3, cells were drug treated for 24 h (HMECs) or 96 h (ARPE-19 cells) with 0.1% DMSO or 10 μM to 90 μM of each compound 4, 8, 15, 18 or 20, with 4 replicate wells of each compound. After 24-96 h, cells were incubated with 10 μM 5 mg/ml MTT labelling Reagent (Roche) for 2 h. Subsequently, when purple formazan crystals formed cells were incubated with 1× solubilisation solution (Roche) for 4 h and absorbance read at 570 nm using a microplate reader.

Figure 9:
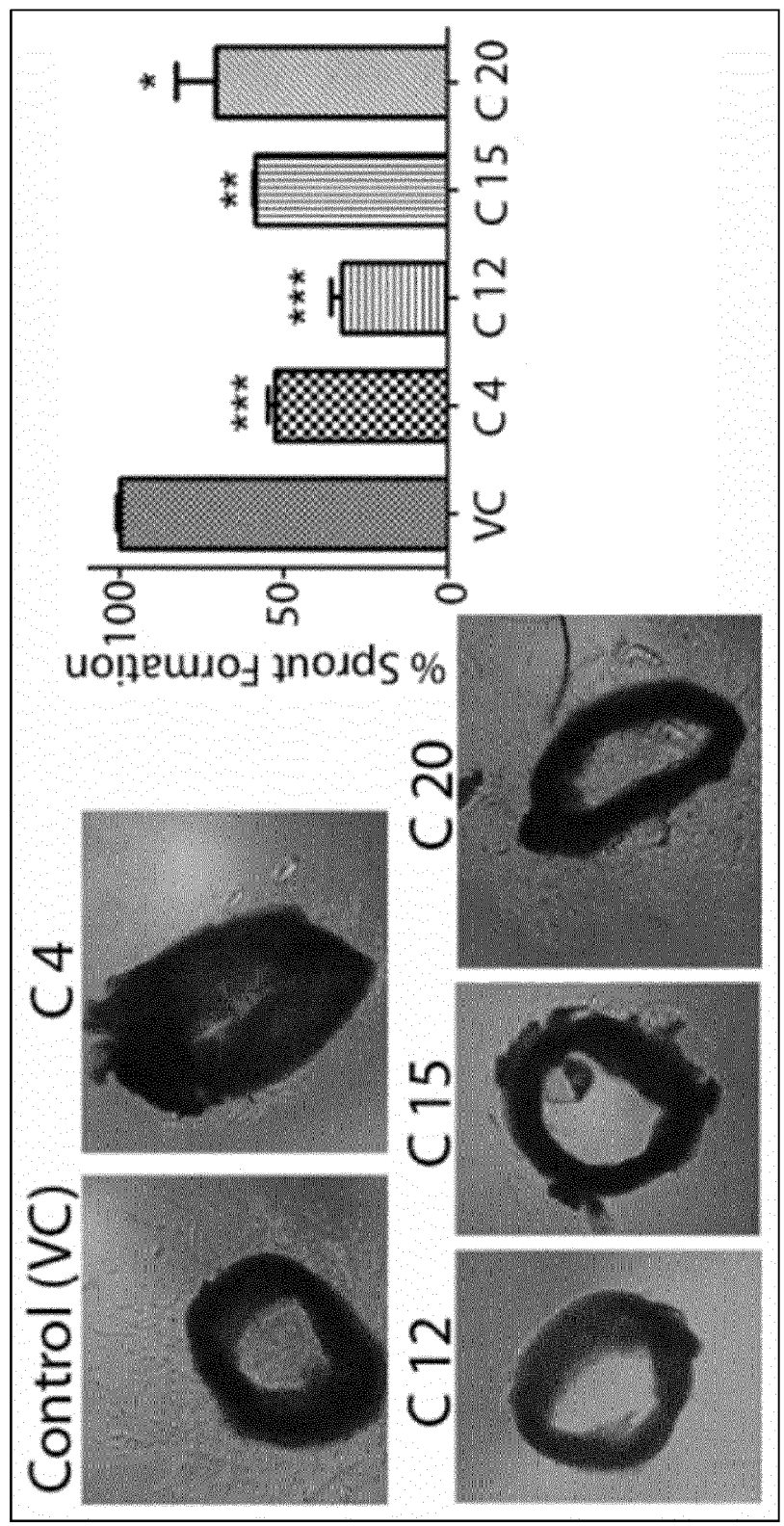
FIG. 9 is a graph (right) and representative murine aortic ring images (left) showing that compounds 4, 12, 15 and 20 block angiogenesis (sprout formation) in the mouse aortic ring assay. The results are the mean of 2 independent experiments for compounds 12 and 15, for all other treatments the results are the mean of 3 independent experiments. *P<0.05, **P<0.01. Data shown is mean+SEM.

Example 7—Quantification of Anti-Angiogenic Activity in an Ex Vivo Mouse Aortic Ring Model. (FIG. 9)

Aortae from sex matched C57/BL6 littermates were cleansed of adipose tissue, cut into 2 mm rings and immersed in matrigel. Aortic rings (6 per experiment) were treated with 0.1% DMSO (vehicle control/VC) or with 10 μM of Compound 4, Compound 12, Compound 15 or Compound 20. Sprouts from the perimeter of the aortic ring were counted and quantified as percentage of vehicle control (VC). Compounds 4, 12, 15 and 20 inhibit the formation of sprouts in a statistically significant manner.

Figure 10:
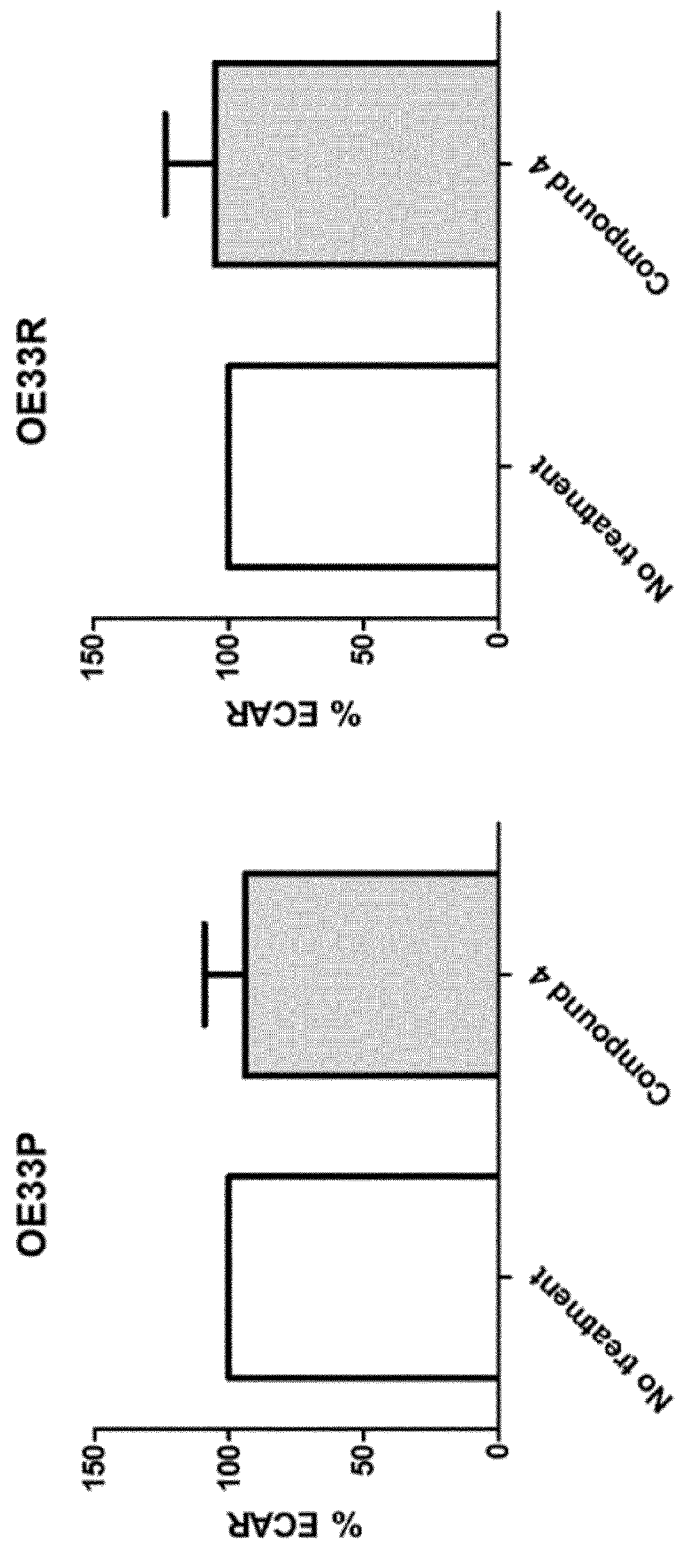
FIG. 10 is a pair of graphs showing that compound 4 does not significantly reduce extraceullar acidification rate (ECAR), a measure of glycolysis, in OE33P radiosensitive (left graph) or in OE33R radioresistant (right graph) oesophageal adenocarcinoma cells. OE33P and OE33R cells were treated with 10 µM of compound 4 for 24 hours, then Seahorse Bioscience metabolism technology was conducted (n=7).

Example 8—Compound 4 does not Significantly Reduce Glycolysis of Human OE33P or OE33R Cells In Vitro. (FIG. 10)

OE33P radiosensitive oesophageal adenocarcinoma cells and OE33R radioresistant oesophageal adenocarcinoma cells were used to test the effects of the compound 4 on glycolysis. Cells were maintained in RPMI media supplemented with 10% foetal calf serum, penicillin (100 U/ml) and streptomycin (100 μg/ml). A total of 11,000 cells (OE33P) or 13,000 cells (OE33R), in 100 μl media, were seeded per well in 24 well plates and left to incubate for 24 hours, with an additional 150 μl media added after 5 hours. The media was replaced with solutions containing 10 μM of compound 4 or the equivalent volume of DMSO vehicle control. After 24 hours of treatment, media was replaced with modified DMEM supplemented with 0.5 mM glucose. Rates of glycolysis were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 595 nm Rates of glycolysis were then normalised to cell number.

Figure 11:
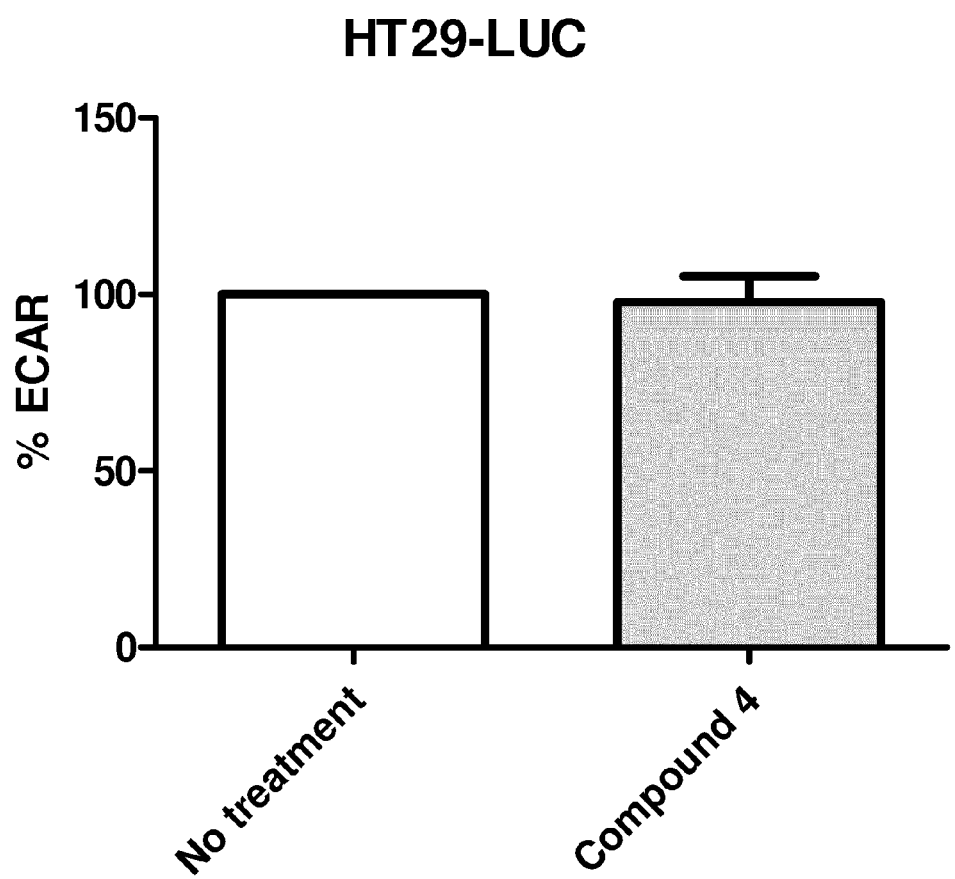
FIG. 11 is a graph showing that compound 4 does not significantly reduce extraceullar acidification rate (ECAR), a measure of glycolysis, in HT29-LUC radioresistant colorectal adenocarcinoma cells. HT29-LUC were treated with 10 µM of compound 4 for 24 hours, then Seahorse Bioscience metabolism technology was conducted (n=5).

Example 9—Compound 4 does not Significantly Reduce Glycolysis of Human HT29-LUC Cells In Vitro. (FIG. 11)

HT29-LUC radioresistant colorectal adenocarcinoma cells were used to test the effects of compound 4 on glycolysis. Cells were maintained in McCoy's 5A media supplemented with 10% foetal calf serum. A total of 20,000 cells, in 100 µl media, were seeded per well in 24 well plates and left to incubate for 24 hours, with an additional 150 µl media added after 5 hours. The media was replaced with solutions containing 10 µM of compound 4 or the equivalent volume of DMSO vehicle control. After 24 hours of treatment, media was replaced with modified DMEM supplemented with 0.5 mM glucose. Rates of glycolysis were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 595 nm Rates of glycolysis were then normalised to cell number.

Figure 12:
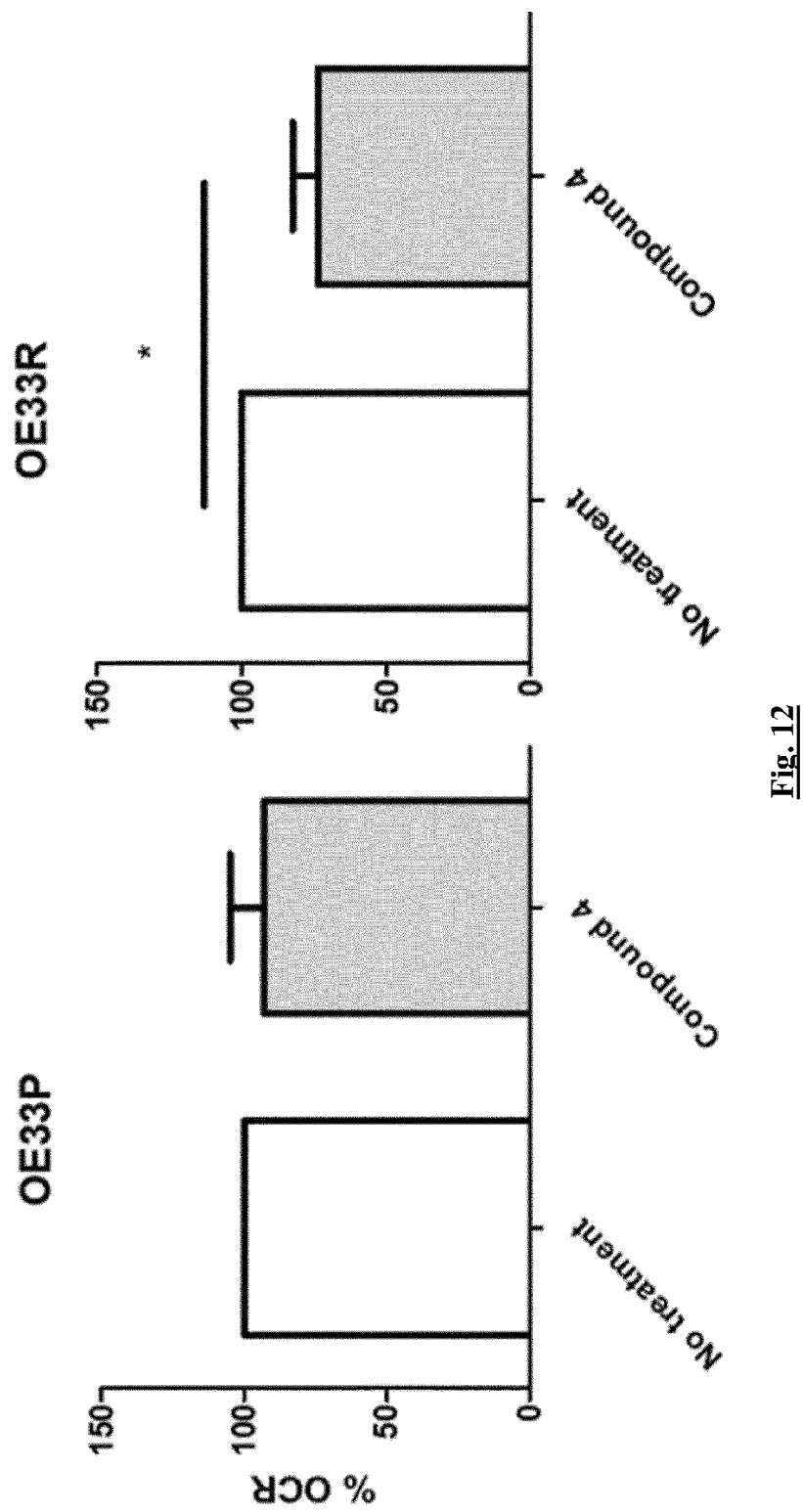
FIG. 12 is a pair of graphs showing that compound 4 does not significantly reduce oxygen consumption rate (OCR), a measure of oxidative phosphorylation, in OE33P radiosensitive (left graph) but does significantly reduce OCR in OE33R radioresistant (right graph) oesophageal adenocarcinoma cells (p<0.05). OE33P and OE33R cells were treated with 10 µM of compound 4 for 24 hours, then Seahorse Bioscience metabolism technology was conducted (n=7).

Example 10—Rates of Oxidative Phosphorylation are not Significantly Different Between Human OE33P and OE33R Cells Treated with Compound 4 In Vitro. (FIG. 12)

OE33P radiosensitive and OE33R radioresistant oesophageal adenocarcinoma cells were used to test the effects of the compound 4 on oxidative phosphorylation. Cells were maintained in RPMI media supplemented with 10% foetal calf serum, penicillin (100 U/ml) and streptomycin (100 µg/ml). A total of 11,000 OE33P cells and 13,000 OE33R cells, in 100 µl media, were seeded per well in 24 well plates and left to incubate for 24 hours, with an additional 150 µl media added after 5 hours. The media was replaced with solutions containing 10 µM of compound 4 or the equivalent volume of DMSO vehicle control. After 24 hours of treatment, media was replaced with modified DMEM supplemented with 0.5 mM glucose. Rates of oxidative phosphorylation were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 595 nm Rates of oxidative phosphorylation were then normalised to cell number.

Figure 13:
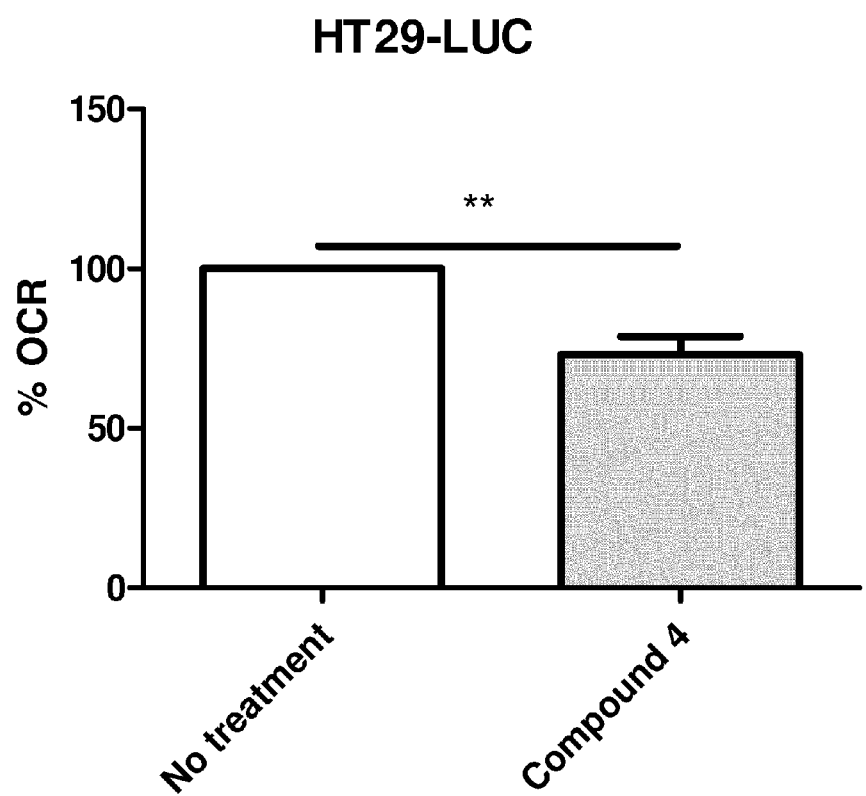
FIG. 13 is a graph showing that compound 4 significantly reduces oxygen consumption rate (OCR), a measure of oxidative phosphorylation, in HT29-LUC radioresistant colorectal adenocarcinoma cells (p<0.01). HT29-LUC were treated with 10 µM of compound 4 for 24 hours, then Seahorse Bioscience metabolism technology was conducted (n=5).

Example 11—Compound 4 Significantly Reduces Oxidative Phosphorylation of Human HT29-LUC Cells In Vitro. (FIG. 13)

HT29-LUC radioresistant colorectal adenocarcinoma cells were used to test the effects of the compound 4 on oxidative phosphorylation. Cells were maintained in McCoy's 5A media supplemented with 10% foetal calf serum. A total of 20,000 cells, in 100 µl media, were seeded per well in 24 well plates and left to incubate for 24 hours, with an additional 150 µl media added after 5 hours. The media was replaced with solutions containing 10 µM of compound 4 or the equivalent volume of DMSO vehicle control. After 24 hours of treatment, media was replaced with modified DMEM supplemented with 0.5 mM glucose. Rates of oxidative phosphorylation were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 595 nm Rates of oxidative phosphorylation were then normalised to cell number.

Figure 14:
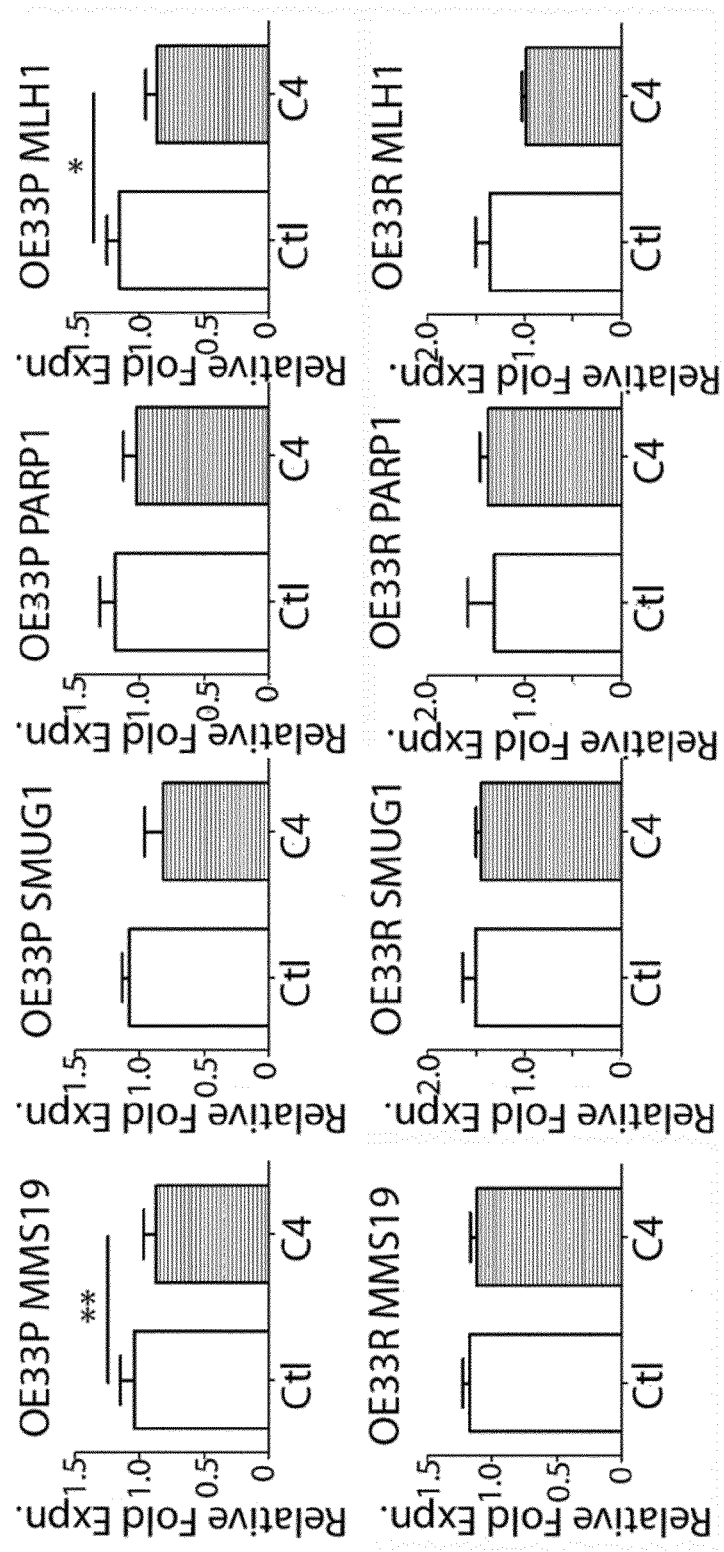
FIG. 14 is a set of graphs showing that compound 4 significantly reduces the expression of MMS19 (p<0.01) and MLH1 (p<0.05) in OE33P radiosensitive oesophageal adenocarcinoma cells. Expression of SMUG1 and PARP1 in OE33P were not significantly different to control. Expression of SMUG1, PARP1, MMS19 and MLH1 were not significantly different to control in OE33R radioresistant oesophageal adenocarcinoma cells. OE33P and OE33R were treated with 10 µM of compound 4 for 24 hours, RNA was extracted from cells and converted to cDNA which was used in qPCR to examine gene expression (n=3).

Example 12—Compound 4 Significantly Reduces Expression of MMS19 and MLH1 in Human OE33P Cells In Vitro. (FIG. 14)

Figure 15:
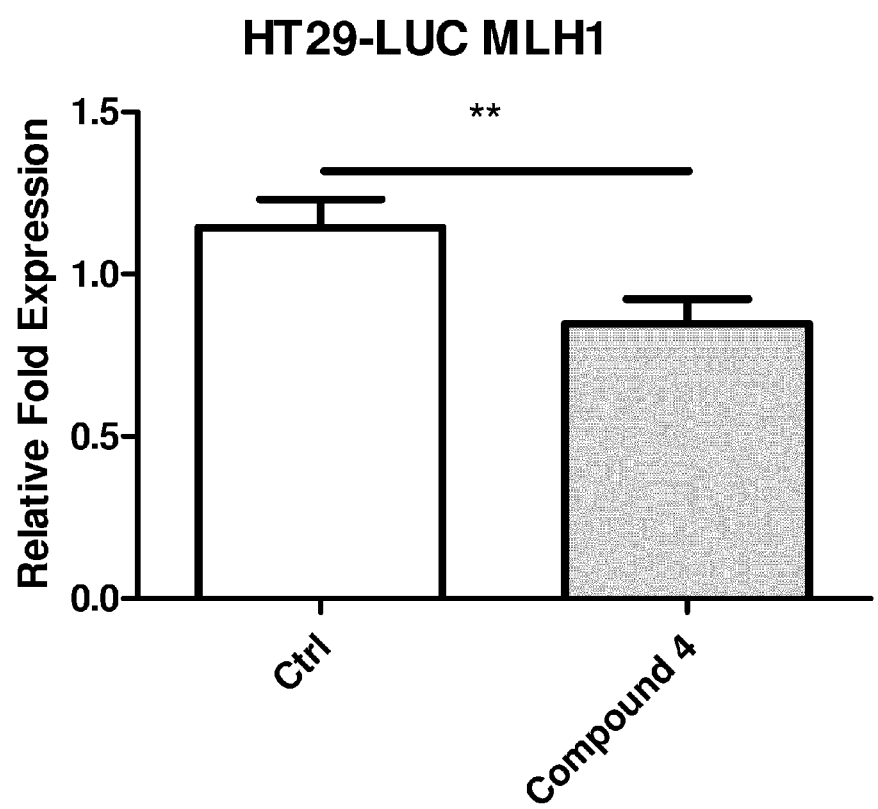
FIG. 15 is a graph showing that compound 4 significantly reduces the expression of MLH1 (p<0.01) in HT29-LUC radioresistant colorectal adenocarcinoma cells. HT29-LUC were treated with 10 µM of compound 4 for 24 hours, RNA was extracted from cells and converted to cDNA which was used in qPCR to examine gene expression (n=3).

OE33P radiosensitive oesophageal adenocarcinoma cells and OE33R radioresistant oesophageal adenocarcinoma cells were used to test the effects of the compound 4 on DNA repair gene expression. Cells were maintained in RPMI media supplemented with 10% foetal calf serum, penicillin (100 U/ml) and streptomycin (100 µg/ml). A total of 300,000 cells, in 2 ml media, were seeded per well in 6 well plates and left to incubate for 24 hours. The media was replaced with solutions containing 10 µM of compound 4 or the equivalent volume of DMSO vehicle control. After 24 hours of treatment, RNA was extracted from the cells and converted to cDNA. qPCR was then conducted and expression of MMS19, SMUG1 PARP1 and MLH1 was quantified, Example 13—Compound 4 Significantly Reduces Expression of MLH1 in Human HT29-LUC Cells In Vitro. (FIG. 15)

HT29-LUC radioresistant colorectal adenocarcinoma cells were used to test the effects of the compound 4 on DNA repair gene expression. Cells were maintained in McCoy's 5A media supplemented with 10% foetal calf serum. A total of 300,000 cells, in 2 ml media, were seeded per well in 6 well plates and left to incubate for 24 hours. The media was replaced with solutions containing 10 µM of compound 4 or the equivalent volume of DMSO vehicle control. After 24 hours of treatment, RNA was extracted from the cells and converted to cDNA. qPCR was then conducted.

Figure 16:
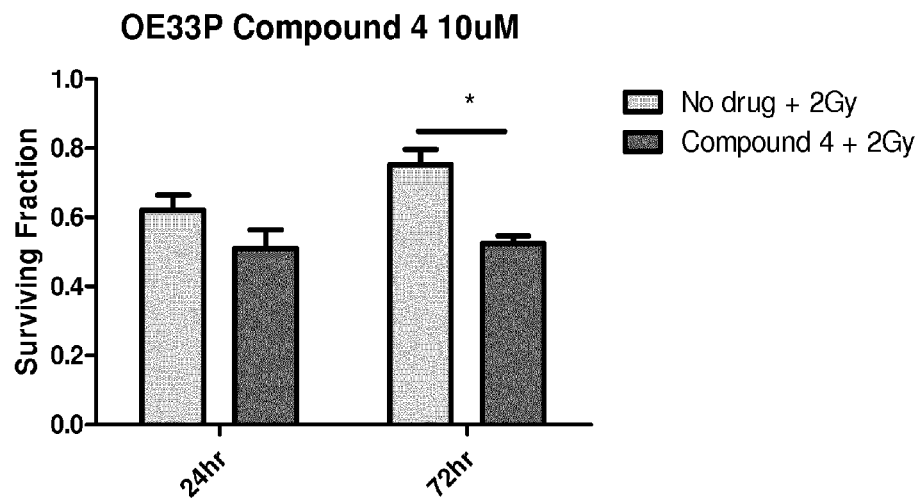
FIG. 16 is a graph showing surviving fraction of OE33P radiosensitive oesophageal adenocarcinoma cells when cells were treated with 10 µM Compound 4 and 2Gy radiation. OE33P were treated with 10 µM of Compound 4 for 24 and 72 hours, irradiated with 2Gy radiation and left until control colonies were sufficiently large.

Example 14—Surviving Fraction of Human OE33P Cells In Vitro when Cells were Treated with Compound 4 and 2Gy Radiation. (FIG. 16)

OE33P radiosensitive oesophageal adenocarcinoma cells were used to test the effects of compound 4 on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The media was replaced with solutions containing 10 µM of compound 4 or the equivalent volume of DMSO vehicle control. After 24 and 72 hours of treatment, media was replaced and the cells were subjected to 2Gy radiation. When control colonies had grown sufficiently large, the media was disposed and the cells washed with PBS. The cells were fixed with methanol and stained with crystal violet. Surviving fraction, the ability of the cells to form colonies was then determined.

Figure 17:
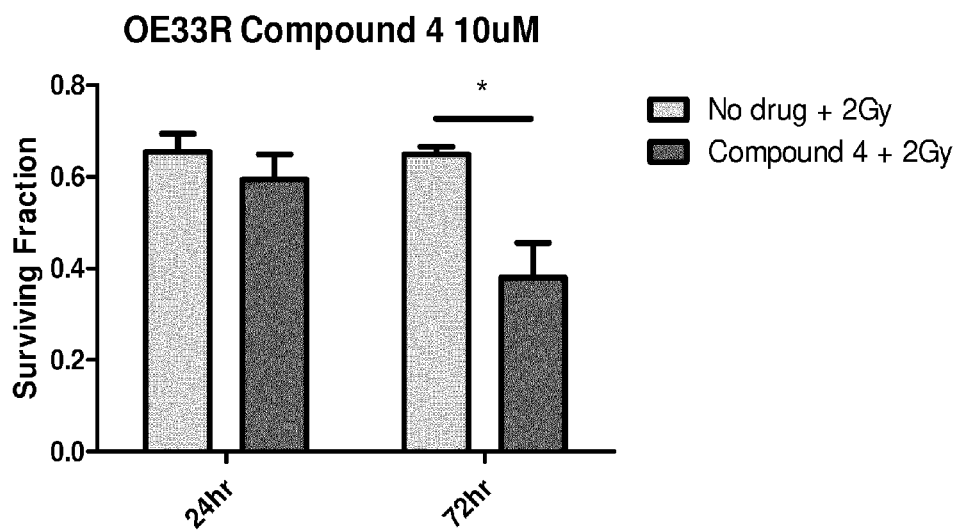
FIG. 17 is a graph showing surviving fraction of OE33R radioresistant oesophageal adenocarcinoma cells when cells were treated with 10 µM Compound 4 and 2Gy radiation. OE33R were treated with 10 µM of Compound 4 for 24 and 72 hours, irradiated with 2Gy radiation and left until control colonies were sufficiently large.

Example 15—Surviving Fraction of Human OE33R Cells In Vitro when Cells were Treated with Compound 4 and 2Gy Radiation. (FIG. 17)

OE33R radioresistant oesophageal adenocarcinoma cells were used to test the effects of compound 4 on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The media was replaced with solutions containing 10 µM of compound 4 or the equivalent volume of DMSO vehicle control. After 24 and 72 hours of treatment, media was replaced and the cells were subjected to 2Gy radiation. When control colonies had grown sufficiently large, the media was disposed and the cells washed with PBS. The cells were fixed with methanol and stained with crystal violet. Surviving fraction, the ability of the cells to form colonies was then determined.

Figure 18:
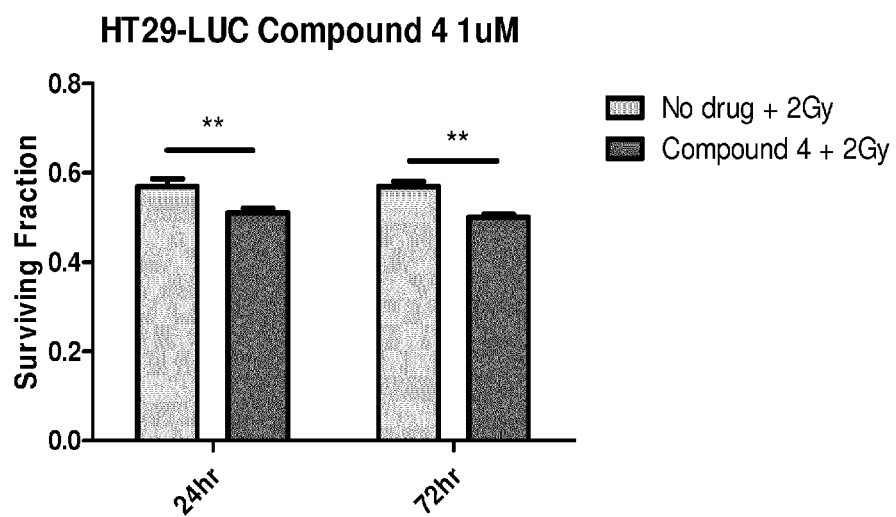
FIG. 18 is a graph showing surviving fraction of HT29-LUC radioresistant colorectal adenocarcinoma cells when cells were treated with 1 µM Compound 4 and 2Gy radiation. HT29-LUC were treated with 1 µM of Compound 4 for 24 and 72 hours, irradiated with 2Gy radiation and left until control colonies were sufficiently large.

Example 16—Surviving Fraction of Human HT29-LUC Cells In Vitro when Cells were Treated with Compound 4 and 2Gy Radiation. (FIG. 18)

HT29-LUC radioresistant colorectal adenocarcinoma cells were used to test the effects of compound 4 on cell survival. Cells were maintained in McCoy's 5A media supplemented with 10% foetal calf serum. Cells were seeded in 6 well plates and left to incubate for 24 hours. The media was replaced with solutions containing 1 μM of compound 4 or the equivalent volume of DMSO vehicle control. After 24 and 72 hours of treatment, media was replaced and the cells were subjected to 2Gy radiation. When control colonies had grown sufficiently large, the media was disposed and the cells washed with PBS. The cells were fixed with methanol and stained with crystal violet. Surviving fraction, the ability of the cells to form colonies was then determined.

Figure 19:
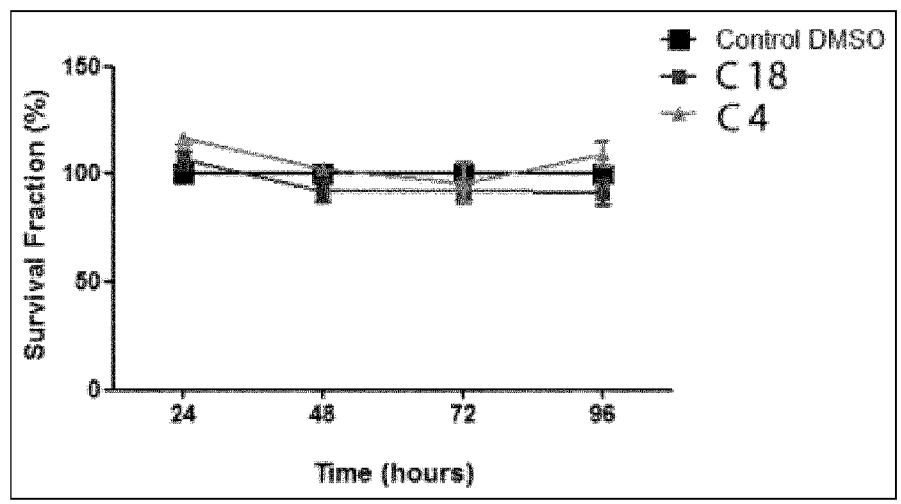
FIG. 19 is a graph showing that treatment with compound 4, or 18 does not affect cell viability in a clonogenic assay at 24-96 hours in human HT29-Luc2 cells. HT29-Luc2 cells were treated with 0.1% DMSO or 10 µM compound 4 or 18. N=3. Data shown is mean+SEM.

Example 17—Quantification of Cell Viability in Human HT29-Luc2 Cells Using a Clonogenic Assay. (FIG. 19)

HT29-Luc2 CRC cells were maintained using McCoy's 5A (Gibco 36600-088) medium supplemented with 10% FBS (Gibco 10270-106) at 37° C./5% CO2. Cells were washed in DPBS and trypsinised using 2 ml TrypLE™ Express (1×) (Invitrogen). Cells were centrifuged following detachment at 1200 rpm for 4 minutes. The cell pellet was resuspended in full media and a cell count was performed using a haemocytometer. $1.5 \times 10^3$ cells were seeded per well of a 6 well plate and left to adhere for 24 hours. Cells were then treated with 10 μM of compound 4 or 18 for 24 hours. The drugs were then removed and cells were allowed to grow in fresh media for 10 days in total, clones were then fixed using 4% paraformaldehyde and stained by incubating with 0.5% crystal violet solution (Pro-Lab diagnostics PL.7000) at RT for 2 hours. Clones counting was performed using the ColCount™ system (Oxford Optronix).

Figure 20:
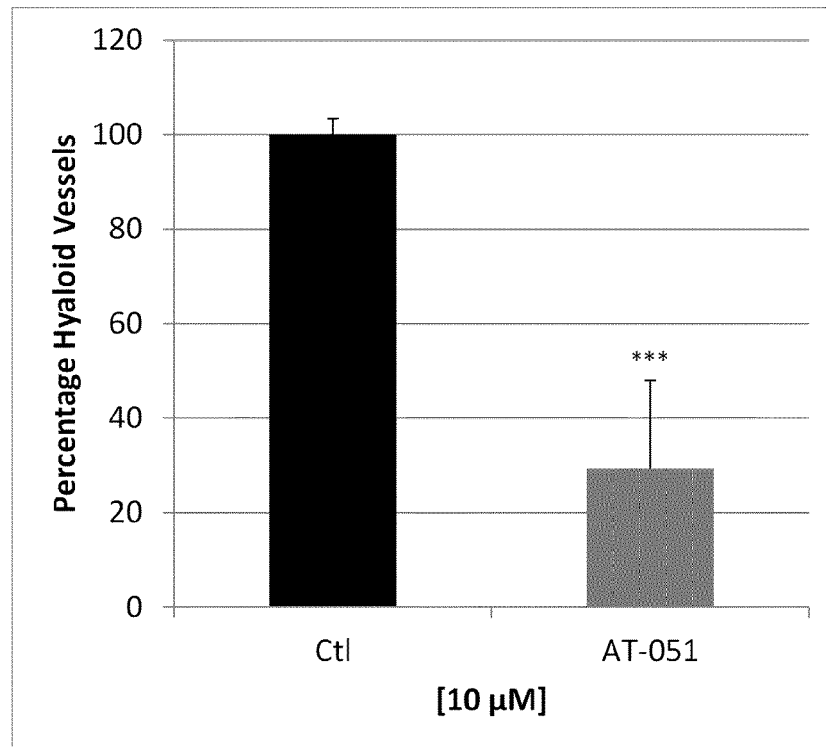
FIG. 20 is a pair of graphs showing that compound AT-051/41206012 purchased from Specs (Netherlands) significantly inhibits developmental angiogenesis of zebrafish hyaloid vessels (n=5, ***p-value≤0.001; top graph) but does not inhibit developmental angiogenesis of the intersegmental vessels (n=6; bottom graph). The chemical name of AT-051/41206012 is 2-[2-(2-methoxyphenyl)ethenyl]pyrazine.
Figure 20:
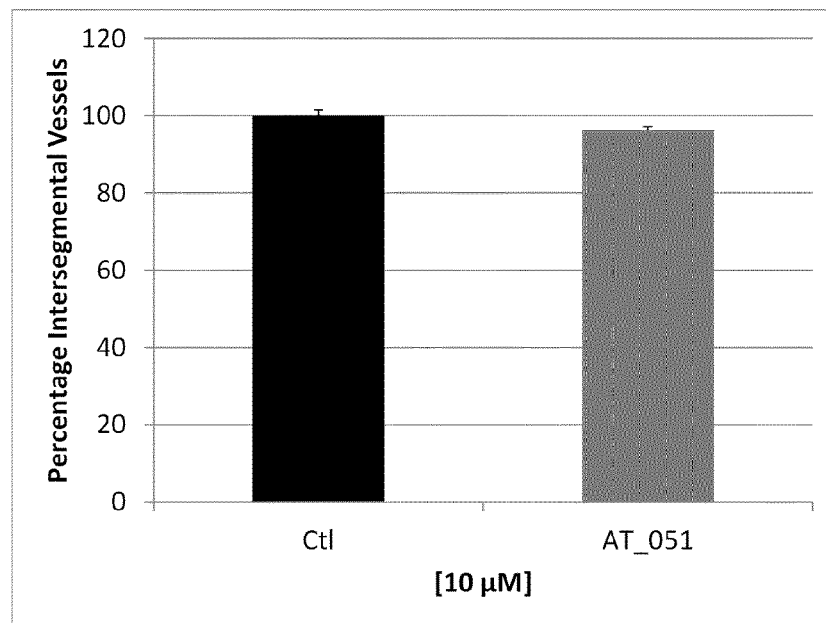

Example 18—Quantification of Primary Hyaloid Vasculature Branches and Intersegmental Vessels in AT-051-Treated Zebrafish. (FIG. 20)

All experimental protocols were carried out as per example 1 and 2. Briefly, zebrafish larvae were treated with 10 μM of AT-051/41206012 (chemical name 2-[2-(2-methoxyphenyl)ethenyl]pyrazine) purchased from Specs (The Netherlands). At 6 or 48 hours post fertilisation (hpf), 5 embryos per well were placed in 400 μl of Embryo Medium/0.1% DMSO and incubated with 10 μM AT-051/41206012 at 28° C. on a 14 h light/10 h dark cycle. Larvae were treated from 6-48 hpf (intersegmental vessel study) or from 48 to 120 hpf (primary hyaloid vessel study). At the end of the study, larvae were euthanized and fixed in 4% PFA at 4° C. overnight before analysis.

The number of intersegmental vessels was counted and the average number was graphed for each drug. Right lenses were dissected from the larvae and transferred to depression slides for observation and the number of primary hyaloid vessels radiating from the back of the lens (3-4 main branches at 5 dpf in controls and previously described), was counted and the average number was graphed for each drug. AT-051/41206012 does not affect the development of intersegmental vessels but does inhibit developmental angiogenesis of the zebrafish hyaloid vasculature in a statistically significant manner at 10 μM drug concentration.

Oesophageal Cancer is the $6^{th}$ most common cause of cancer related deaths worldwide.

Globally, there has been a dramatic epidemiological increase in the incidence of oesophageal adenocarcinoma (OAC), with Ireland showing a 48% increase in incidence rates over the last 3 years. Rising increase in obesity levels strongly correlates with the dramatic increases in the number of OAC cases. 5 year survival rates are approximately 10%. Treatment options for these patients are limited. 70% of OAC patients receive a treatment called 'neoadjuvant treatment' meaning they will be treated with a combination of radiation and chemotherapy prior to their surgery. The goal of this treatment is to downsize the tumour in order to make surgery more successful. This is a 6 week treatment that can have many negative side effects for the patients. Unfortunately, only approximately 25% of the patients will respond to this treatment. Therefore approximately 75% of patients receive this treatment, suffer the negative side effects and importantly they will experience a significant delay to surgery which may impact on their overall survival rates. These patients are referred to as 'non responders' Work done by the Department of Surgery at Trinity College Dublin (J Mol Med (2012) 90:1449-1458) has shown that these non responders show high levels of metabolism (energy production) and high levels of DNA repair protein expression. The high level of DNA repair protein expression tries to repair the damaged DNA following radiation and therefore prevents the radiated cells from undergoing cell death.

We have found that the compounds described above can reduce metabolism rates and expression of DNA repair proteins in cancer cells, resulting in a reduced number of surviving cancer cells. These compounds may have clinical utility in not only non responders but also for those tumours that are sensitive to radiation, they may further increase response in this subset of patients also. This neoadjuvant treatment is not specific to OAC; it also applies to colorectal cancer and breast cancer.

The disclosures of the various references mentioned in this specification are hereby incorporated by reference in their entirety.

The invention is not limited to the embodiments hereinbefore described, accompanying which may be varied in detail.

REFERENCES

Alvarez Y, Astudillo O, Jensen L, Reynolds A L, Waghorne N, Brazil D P, Cao Y, O'Connor J J, Kennedy B N. 2009. Selective inhibition of retinal angiogenesis by targeting PI3 kinase. PLoS One 4:e7867.

Alvarez Y, Cederlund M L, Cottell D C, Bill B R, Ekker S C, Torres-Vazquez J, Weinstein B M, Hyde D R, Vihtelic T S, Kennedy B N. 2007. Genetic determinants of hyaloid and retinal vasculature in zebrafish. BMC Dev Biol 7:114.

Bergers G, Benjamin L E. 2003. Tumorigenesis and the angiogenic switch. Nat Rev Cancer 3:401-410.

Bergers G, Hanahan D. 2008. Modes of resistance to anti-angiogenic therapy. Nat Rev Cancer 8:592-603.

Brockerhoff S E. 2006. Measuring the optokinetic response of zebrafish larvae. Nat Protoc 1:2448-2451.

Carmeliet P. 2005. VEGF as a key mediator of angiogenesis in cancer. Oncology 69 Suppl 3:4-10.
Culy C. 2005. Bevacizumab: antiangiogenic cancer therapy. Drugs Today (B arc) 41:23-36.
den Hertog J. 2005. Chemical genetics: Drug screens in Zebrafish. Biosci Rep 25:289-297.
Doukas J, Mahesh S, Umeda N, Kachi S, Akiyama H, Yokoi K, Cao J, Chen Z, Dellamary L, Tam B, Racanelli-Layton A, Hood J, Martin M, Noronha G, Soll R, Campochiaro P A. 2008. Topical administration of a multi-targeted kinase inhibitor suppresses choroidal neovascularization and retinal edema. J Cell Physiol 216:29-37.
Ellis L M. 2003. Antiangiogenic therapy at a crossroads: clinical trial results and future directions. J Clin Oncol 21:281s-283s.
Ferrara N. Vascular endothelial growth factor and age-related macular degeneration: from basic science to therapy. Nat Med 16:1107-1111.
Ferrara N, Kerbel R S. 2005. Angiogenesis as a therapeutic target. Nature 438:967-974 Frank R N. 2004. Diabetic retinopathy. N Engl J Med 350:48-58.
Goldsmith P. 2004. Zebrafish as a pharmacological tool: the how, why and when. Curr Opin Pharmacol 4:504-512.
He A R, Marshall J. 2005. Biologic therapy for colon cancer. Clin Adv Hematol Oncol 3:555-561.
Jager R D, Mieler W F, Miller J W. 2008. Age-related macular degeneration. N Engl J Med 358:2606-2617.
Kleinman M E, Yamada K, Takeda A, Chandrasekaran V, Nozaki M, Baffi J Z, Albuquerque R J, Yamasaki S, Itaya M, Pan Y, Appukuttan B, Gibbs D, Yang Z, Kariko K, Ambati B K, Wilgus T A, DiPietro L A, Sakurai E, Zhang K, Smith J R, Taylor E W, Ambati J. 2008. Sequence- and target-independent angiogenesis suppression by siRNA via TLR3. Nature 452:591-597.
MacRae C A, Peterson R T. 2003. Zebrafish-based small molecule discovery. Chem Biol 10:901-908.
Mandala M, Ferretti G, Barni S. 2004. Oxaliplatin in colon cancer. N Engl J Med 351:1691-1692; author reply 1691-1692.
Narayanan R, Kuppermann B D, Jones C, Kirkpatrick P. 2006. Ranibizumab. Nat Rev Drug Discov 5:815-816.
Peterson R T, Shaw S Y, Peterson T A, Milan D J, Zhong T P, Schreiber S L, MacRae C A, Fishman M C. 2004. Chemical suppression of a genetic mutation in a zebrafish model of aortic coarctation. Nat Biotechnol 22:595-599.
Pichler F B, Laurenson S, Williams L C, Dodd A, Copp B R, Love D R. 2003. Chemical discovery and global gene expression analysis in zebrafish. Nat Biotechnol 21:879-883.
Rattner A, Nathans J. 2006. Macular degeneration: recent advances and therapeutic opportunities. Nat Rev Neurosci 7:860-872.
Takahashi K, Saishin Y, Saishin Y, King A G, Levin R, Campochiaro P A. 2009. Suppression and regression of choroidal neovascularization by the multitargeted kinase inhibitor pazopanib. Arch Ophthalmol 127:494-499.
Wong S F. 2005. Cetuximab: an epidermal growth factor receptor monoclonal antibody for the treatment of colorectal cancer. Clin Ther 27:684-694.
Zon L I, Peterson R T. 2005. In vivo drug discovery in the zebrafish. Nat Rev Drug Discov 4:35-44.

The invention claimed is:
1. A method for the treatment of an angiogenesis related disease or disorder comprising the step of administering a compound of the formula

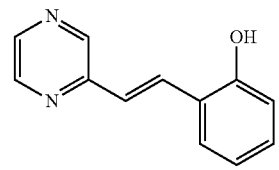 [SMILES: Oc1ccccc1/C=C/c1cnccn1]

or a salt thereof.

2. The method as claimed in claim 1, wherein the angiogenesis-related disease or disorder is associated with neovascularisation of the eye.

3. The method as claimed in claim 1, wherein the angiogenesis-related disease or disorder is associated with blindness.

4. The method as claimed in claim 1, wherein the angiogenesis-related disease or disorder is age-related macular degeneration or diabetic retinopathy.

5. The method as claimed in claim 4, wherein the age-related macular degeneration is wet age-related macular degeneration.

6. The method as claimed in claim 1, wherein the angiogenesis-related disease or disorder is cancer.

7. The method as claimed in claim 6, wherein the cancer is a solid tumour forming cancer.

8. The method as claimed in claim 6, wherein the cancer is colorectal cancer.

9. The method as claimed in claim 6, wherein the cancer is oesophageal cancer.

10. The method as claimed in claim 6, wherein the cancer is breast cancer.

* * * * *